United States Patent [19]
Phillips et al.

[11] Patent Number: 5,135,549
[45] Date of Patent: Aug. 4, 1992

[54] CHROMATOGRAPHIC TECHNIQUE AND APPARATUS

[75] Inventors: John B. Phillips, Carbondale, Ill.; Zaiyou Liu, Provo, Utah

[73] Assignee: The Board of Trustees of Southern Illinois University, Carbondale, Ill.

[21] Appl. No.: 647,790

[22] Filed: Jan. 30, 1991

[51] Int. Cl.⁵ ............................................. B01D 15/08
[52] U.S. Cl. .......................................... 55/67; 55/197; 55/386; 210/656; 210/198.2
[58] Field of Search .................... 55/67, 197, 208, 386, 55/18-21; 73/23.22, 23.26, 61.1 C; 210/656, 198.2

[56]     References Cited
        U.S. PATENT DOCUMENTS

| | | | |
|---|---|---|---|
| 2,398,818 | 4/1946 | Turner | 55/197 |
| 2,416,482 | 2/1947 | Holmes | 55/197 |
| 3,043,127 | 7/1962 | De Ford et al. | 55/67 X |
| 3,057,183 | 10/1962 | De Ford | 55/197 X |
| 3,063,286 | 11/1962 | Nerheim | 55/197 X |
| 3,150,516 | 9/1964 | Linnenbom et al. | 55/197 X |
| 3,156,548 | 11/1964 | Perry | 55/197 |
| 3,225,520 | 12/1965 | Burow | 55/197 X |
| 3,225,521 | 12/1965 | Burow | 55/197 X |
| 3,236,603 | 2/1966 | Durrett et al. | 55/197 X |
| 3,449,938 | 6/1969 | Giddings | 55/67 X |
| 3,608,273 | 9/1971 | Fabuss et al. | |
| 3,782,078 | 1/1974 | Jerpe | 55/197 |
| 3,881,892 | 5/1975 | Gehrke et al. | 55/197 X |
| 3,920,420 | 11/1975 | Valentin et al. | 55/197 X |
| 3,926,589 | 12/1975 | Klementi et al. | 55/67 |
| 4,019,863 | 4/1977 | Jenkins et al. | |
| 4,554,436 | 11/1985 | Chlasta et al. | 55/386 X |
| 4,719,011 | 1/1988 | Shalon et al. | 55/386 X |
| 4,726,822 | 2/1988 | Caks et al. | 55/197 X |
| 4,774,190 | 9/1988 | Weiss | 55/197 |
| 4,923,486 | 5/1990 | Rubey | 55/197 X |
| 4,935,145 | 6/1990 | Cortes et al. | 55/67 X |

FOREIGN PATENT DOCUMENTS

| | | | |
|---|---|---|---|
| 2629048 | 1/1977 | Fed. Rep. of Germany | 55/197 |
| 2823445 | 12/1979 | Fed. Rep. of Germany | 55/197 |
| 59-221664 | 12/1984 | Japan | 55/67 |
| 62-190464 | 8/1989 | Japan | 55/67 |

OTHER PUBLICATIONS

J. Q. Walker et al., *Analytical Chemistry*, vol. 42, No. 13, Nov. 1970, pp. 1652–1654.
W. J. Baker et al., *Control Engineering*, Jan. 1961, pp. 77–81.
Paul D. Koons et al., *Hydrocarbon Processing & Petroleum Refiner*, Apr. 1963, vol. 42, No. 4, pp. 133–135.
S. A. Greene et al., *Analytical Chemistry*, vol. 28, No. 9, Sep. 1956, pp. 1369 & 1370.
J. S. Lewis et al., *Analytical Chemistry*, vol. 28, No. 9, Sep. 1956, pp. 1370 & 1371.
"Automated Instrumentation for Comprehensive Two-Dimensional High-Performance Liquid Chromatography of Proteins", M. Bushey et al., *Anal. Chem.* 1990, vol. 62, pp. 161–167.

(List continued on next page.)

*Primary Examiner*—Robert Spitzer
*Attorney, Agent, or Firm*—Watson, Cole, Grindle & Watson

[57]     ABSTRACT

To provide a compact, sensitive comprehensive, two-dimensional gas chromatograph, a chromatographic column has first and second sections in series with each other to permit the flow of sample and a carrier through the first section and the second section. The retention time of the second section is less than the band resolution time of the first section. To control the wave fronts between the first and second sections, first and second heaters are positioned to heat and drive off sample collected at the outlet of the first section for collection in the second section and to heat sample collected at the inlet of the second section so that the first heater rapidly drives off sample for collection in the second section and then the second section rapidly drives off sample in a sharp wave front while the first section is accumulating another band for later movement into the second section.

88 Claims, 4 Drawing Sheets

OTHER PUBLICATIONS

"Automated Instrumentation for Comprehensive Two-Dimensional High-Performance Liquid Chromatography/Capillary Zone Electrophoresis", M. Bushey et al., *Anal. Chem.* 1990, vol. 62, pp. 978–984.

Supello Advertisement, p. 3 (date and source unknown).

"Thermal Modulation Boosts GC Sensitivity", *C&EN* Jan. 14, 1985, pp. 62–64.

"Qualitative Gas Chromatographic Analysis Using Two Columns of Different Characteristics", J. Lewis et al., *Analytical Chemistry* 1956, vol. 28, No. 9, pp. 1370–1373.

"Thermal Desorption Modulation as a Replancement for Sample Injection in Very-Small-Diameter Gas Chromatography Capillary Columns", J. Phillips et al., *Journal of Chromatographic Science* 1986, vol. 24, pp. 396–399.

"Multidimensional Gas Chromatography", W. Bertsch, *Journal of High Resolution Chromatography*, University of Alabama, pp. 74–144.

"Two Dimensional Multiplex Gas Chromatography", D. Palovic et al., 1983 *Pittsburgh Conference Book of Abstracts*, No. 797.

"Two Dimensional Multiplex Gas Chromatography", D. Carney, Southern Illinois University, May 1983.

"Comprehensive Two-Dimensional Gas Chromatography using an On-Column Thermal Modulator Interface", Z. Liu et al., *Journal of Chromatographic Science*, 1991, vol. 29, pp. 227–231.

"Large-Volume Sample Introduction into Narrow-Bore Gas Chromatography Columns Using Thermal Desorption Modulation and Signal Averaging", Z. Liu et al., *Journal of Microcolumn Separations*, 1990, vol. 2, No. 1, pp. 33–40.

"High-Speed Gas Chromatography Using an On-Column Thermal Desorption Modulator", Z. Liu et al., *J. Microcolumn Separations*, 1989 vol. 1, No. 5, pp. 249–256.

"Sample Introduction into a 5-um i.d. Capillary Gas Chromatography Column Using an On-Column Thermal Desorption Modulator", Z. Liu et al., *J. Microcolumn Separations*, 1989, vol. 1, No. 3, pp. 159–162.

"High-Capacity Thermal Desorption Modulators for Gas Chromatography", S. Mitra et al., *Journal of Chromatographic Science*, 1988, vol. 26, pp. 620–623.

"Determination of Activity Coefficients of Binary Liquids By Capillary Gas Chromatography with Thermal Desorption Modulation for Direct Headspace Sampling", M. Zhang et al., *Journal of Chromatography*, 1989, vol. 478, pp. 141–147.

"Multiplex Gas Chromatography by Thermal Modulation of a Fused Silica Capillary Column", J. Phillips et al., *Analytical Chemistry*, 1985, vol. 57, pp. 2779–2787.

"Temperature-Controlled High-Speed Microcolumn Liquid CHromatography", K. Jinno, *Analytical Chemistry*, 1985, vol. 57, No. 2 pp. 574–576.

"A Non-Mechanical Chemical Concentration Modulator for Multiplex Gas Chromatography", J. Valentin et al., *Journal of HRC & CC*, 1982, pp. 269–272.

"Thermal Desorption Modulation as a Replacement for Sample Injection in Very-Small-Diameter Gas Chromatography Capillary Columns", J. Phillips et al., *Journal of Chromatographic Science*, 1986, vol. 24, pp. 396–399.

"Electrically Heated Cold Trap Inlet System for High-Speed Gas Chromatography", B. Ewels et al., *Anal. Chem.*, 1985, 57, pp. 2774–2779.

"Use of Multiple Dimensions in Analytical Separations", J. Giddings, *Multidimensional Chromatography Techniques and Applications*, H. Cortes, Ed., p. v–27.

"Two-Dimensional Separations", J. Giddings, *Unified Separation Science*, pp. 123–131.

"Two-Dimensional Measurements Involving Chromatography", M. Kaljurand et al., *Computerized Multiple Input Chromatography*, pp. 59–99.

"Analysis of Flue-Cured Tobacco Essential Oil by Hyphenated Analytical Techniques", B. Gordon et al., *Journal of Chromatographic Science*, 1988, vol. 26, pp. 174–180.

"Cryogenic-focusing, ohmically heated on-column trap for capillary gas chromatography", S. Springston, *Journal of Chromatography*, 1990 vol. 517, pp. 67–75.

"Multi-dimensional chromatography using on-line coupled microcolumn liquid chromatography–capillary gas chromatography for quantitative pesticide residue analysis", H. Cortes et al., *Analytica Chimca Acta*, 1990, vol. 236, pp. 173–182.

"Design and Performance of a Mass-Flow-Modulated Detector for Gas Chromatography", G. Wells, *Journal of Chromatography*, 1985, vol. 319 pp. 263–272.

"Advances in Two-Dimensional GC with Glass Capillary Columns", E. Anderson, *Journal of High Resolution Chromatography & Chromatography Communications*, 1979, vol. 2, pp. 335–338.

"Methods in High Resolution Gas Chromatography. Two-dimensional Techniques", W. Bertsch, *Journal of High Resolution Chromatography & Chromatography Communications*, Aug. 1978, pp. 85–90.

"Methods in High Resolution Gas Chromatography. Two-Dimensional Techniques", W. Bertsch, *Journal of High Resolution Chromatography & Chromatography Communications*, Dec. 1978, pp. 289–299.

"Concepts and Comparisons in Multidimensional Separation", J. Giddings, *Journal of High Resolution Chromatography & Chromatography Communications*, 1987, vol. 10, pp. 319–323.

"Gas Chromatographic Response as a Function of Sample Input Profiel", Reilley et al., *Analytical Chemistry*, Sep. 1962, vol. 34, No. 10, pp. 1198–1213.

"Methods in High Resolution Gas Chromatography. Two-dimensional Techniques", W. Bertsch, *Journal of High Resolution Chromatography & Chromatography Communications*, Oct. 1978, pp. 187–194.

"Multidimensional Separation of Isomeric Species of Chlorinated Hydrocarbons Such as PCB, PCDD, and PCDF", G. Schomburg et al., *Journal of High Resolution Chromatography & Chromatography Communications*, 1985, vol. 8, pp. 395–400.

"Coupling of High-Performance Liquid Chromatography with Capillary Gas Chromatography", K. Grob, Jr., *Journal of Chromatography*, 1984, vol. 295, pp. 55–61.

"Multidimensional Gas Chromatography with Electron Capture Detection for the Determination of Toxic Congeners in Polychlorinated Biphenyl Mixtures", J. Duinker et al., *Anal. Chem.*, 1988, vol. 60, pp. 478–482.

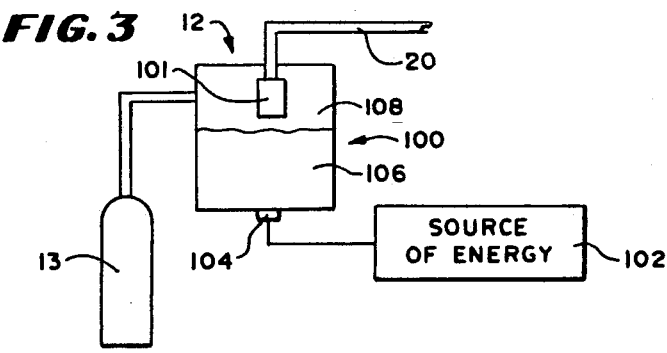
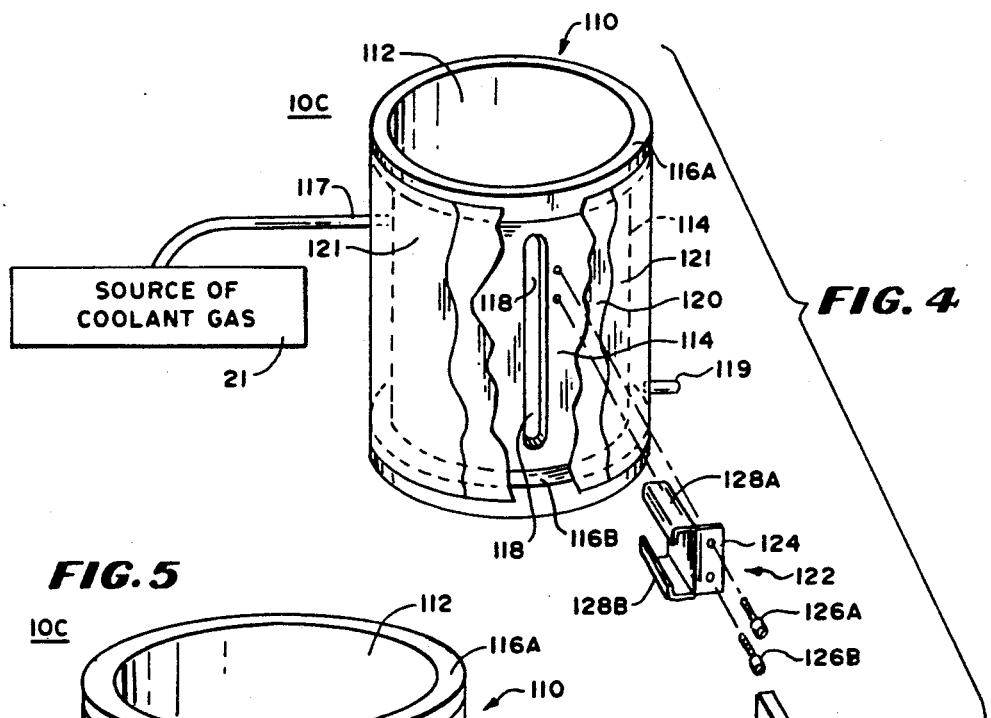
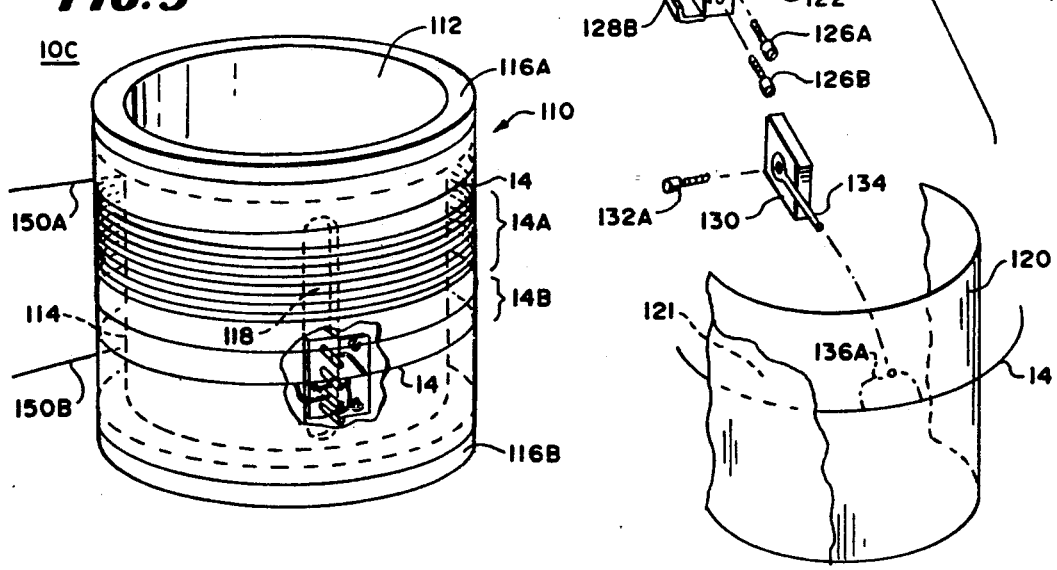

CHROMATOGRAPHIC TECHNIQUE AND APPARATUS

BACKGROUND OF THE INVENTION

This invention relates to chromatographs and chromatographic methods.

PRIOR ART TWO-DIMENSIONAL GAS CHROMATOGRAPHY

In one class of gas chromatography, referred to as two-dimensional gas chromatography, a first and a second column are connected serially with the inlet port of the second column communicating with the outlet of the first column. A sample is injected in the inlet port of the first column and carried through it by a carrier gas. The sample is separated into bands as the sample is carried through the first column. One portion, or in some cases, several portions of the sample from the first column are moved by carrier gas through the second column where further chromatographic separation occurs. Separated components are detected near the outlet opening of the second column.

In a prior art type of two-dimensional gas chromatography, generally referred to as heart-cutting, the first and second columns are two separate columns, with valves between them to permit diversion of vapor stream from the first column before it enters the second column. Generally, the mechanisms used to obtain separation of the components of the sample are similar in the two columns. In using prior art two-dimensional columns, one or more portions of sample eluting from the outlet port of the first column are diverted into the second column. Slices of eluted bands or one to several entire bands are injected into the second column where they are further separated prior to detection.

The prior art heart-cutting two-dimensional chromatography has several disadvantages, such as: (1) not all eluted bands from the first dimension are subjected to the second stage of chromatography; (2) sensitivity is reduced when a secondary chromatographic analysis is performed on only a portion of an eluted band; (3) diversion valving, cooling fluid valving, cold trap heater circuitry, and column interconnections make prior art two-dimensional chromatography complicated and place demand upon the operator; and (4) the time required for chromatographic separation on the second column is comparable to the time required on the first. Long secondary gas-chromatographic analysis time permits at most several "heartcuts" to flow into the second column. The majority of sample bands from the first column may be diverted elsewhere to prevent crossover of bands in the second column.

PRIOR ART THERMAL MODULATION

In another class of gas chromatographic techniques, known as thermal modulation, sample is permitted to accumulate in a relatively cool portion of column, the exterior of which section carries a thin, electrically connected heater, and then released by heating to generate a sharp or spatially compact concentration pulse. In the prior art thermal modulation, a single stage of thermal modulation has been employed on-column. Single stage thermal modulation has also used in connection with two-dimensional gas chromatography. The prior art one-stage thermal modulation technique has the disadvantage of allowing some sample gas to flow through unmodulated during the cooling time of the modulator.

SUMMARY OF THE INVENTION

Accordingly, it is an object of the invention to provide a novel chromatographic technique.

It is a still further object of the invention to provide a novel chromatograph.

It is a still further object of the invention to provide a novel injector for chromatographs.

It is a still further object of the invention to provide a chromatograph which provides rapid and sensitive separation of components of a sample.

It is a still further object of the invention to provide a novel compact and inexpensive chromatograph.

It is a further object of the invention to provide a comprehensive two-dimensional chromatograph.

It is a still further object of the invention to utilize thermal modulation to permit direct online comprehensive two-dimensional chromatography.

COMPREHENSIVE MULTI-DIMENSIONAL GC STRUCTURE

In accordance with the above and further objects of the invention, a chromatographic column has first and second sections either integrally formed with each other or connected to each other in an abutting relationship to permit the flow of sample and a carrier through the first section and the second section. The second section is faster than the first section.

The second section is faster than the first section in the sense that substantially the longest retention time on the column of the second section may be made as short as, or even shorter than, a time interval corresponding to, or characteristic of, unit resolution of chromatographic bands eluting from the column of the first section throughout the duration of a chromatographic separation occuring on the column of the first section.

The increased speed of the second section may be obtained by any of, or a combination of, several structural and operational differences between the first and second sections, such as: (1) the column of the second section may have a substantially smaller diameter than the column of the first, which increases the speed of the second column through combined increases of column efficiency and carrier gas flow velocity; (2) the second column may have higher gas velocity than the first column because of the addition of carrier gas near the outlet of the first column and the inlet of the second; (3) the thickness of the stationary phase in the second column may be less than that of the first column; (4) the second column may be operated at a higher temperature than the first, or, be subjected to a different temperature program than the first; (5) the second column may have imposed upon its longitudinal axis a negative thermal gradient, which in combination with temporal temperature programming, may exert focusing effects which increase the speed of the second column; and (6) the stationary phase of the second column may differ in its chemical composition from that of the first.

In some embodiments, the second column has a retention time which is no more than about 25 percent the retention time of the first column and substantially all sample and a carrier gas flows through both the first and second columns.

MULTI-STAGE THERMAL MODULATION

To produce sharp wave fronts between the first and second columns, a heater is positioned in juxtaposition with the first column or an extension thereof adjacent to the outlet end of the first column and before the inlet end of the second column. Alternative the heater may be positioned in the second column or an extension thereof near its inlet so that sample separated by the first column can be accumulated near the heater and then driven off in a sharp wave front by rapid heating. The retention time of the second column is equal to or less than the band separation time of the first column near the time sample is driven into the second column.

For further effectiveness, a second heater is positioned near the first mentioned heater. Preferably, the first heater is positioned to heat sample collected in the first column or an extension thereof near the outlet of the first column and the second heater is positioned to heat sample collected near the inlet, or an extension thereof, of the second column.

With this arrangement, the first heater becomes hot to rapidly drive off sample and then cools rapidly to resume accumulation of sample from the first column. The same sample that is driven from the first heater section, herein referred to as the first stage, is accumulated at the inlet of the second heater section herein, referred to as the second stage. The second stage then rapidly drives off that sample in a sharp wave front while the first stage is still accumulating sample for later movement into the second stage. The steps of accumulation, transfer between the heater sections and release from the stages are coordinated so that comprehensive modulated collection and transmission of sample eluted from the first column generates a series of sharp wave fronts to be separated in the second column. Collectively, these wave fronts include the entire sample.

In the case of capillary gas chromatography, the stages of this "two-stage thermal modulator" are advantageously portions of the capillary column, externally coated over at least portions of their lengths with resistive coats adapted to serve as electric heaters upon being electrically energized. The modulating stages are separately electrically connected and it may be preferable to have several mutually insulated coats on different positions of the columns, the ends of such coats partially overlapping, each individually electrically connected to circuitry which may program the temperature of each modulating stage.

In the preferred embodiment, the sections of the capillary column system are looped so there are adjacent lengths for the transfer of heat from one to another. To aid in transmitting heat from one length to another, a fluid may move over the coils and a thermally conductive material such as graphite may be applied over the coils of the column.

Advantageously, the loops may be loops of a helix wound around a tubular support member. The pitch of the helical winding may be varied to create and control longitudinal variations in temperature gradients. Electrical contacts may extend through the walls of the tubular support member into its center. The support member may also support the flow of fluid such as gas to carry heat from one length to another. Instead of being wound over a tube, the loops may be bent over a planar surface having a temperature gradient, they may be formed within a solid in a plane, or they may be molded in a substance such as porcelain as a conductor and etched from the porcelain. Instead of controlling heat transfer between loops by spacing alone, the thermal conductivity between loops may also be used.

To make electrical contact between sources of potential, external coats on the two-stage modulators, and coats for thermal gradient control the coat on the capillary may be electrically connected to a similar coat on a supporting surface. In the preferred embodiment, the supporting surface is a thin walled tube or cylindrical sheet having low thermal mass or thermal inertia. This extension of the capillary coat may make electrical contact with electrical connectors. The connectors may be clamp-type electrical connectors, probes or solder connectors preferably protruding from the inner side of the tube to the outside, in those embodiments in which a tube support is used. Ideally, portions of the tube support should be removed to reduce the effective thermal mass which must be heated by the modulator sections. Thus, the modulator stage makes physical contact with the thin walled tube only at or near the ends of the modulator. In some embodiments, cooling exposed stages of the two-stage modulator may be accelerated by placement of a Peltier heat pump in close proximity thereto.

The first and second sections of the capillary column system may be: (1) drawn separately, each to a different diameter; or (2) drawn as one continuous tube in two sections having different size inner diameters. If drawn separately, the sections may be connected after they are drawn with a butt connection having a tube over the two sections or they may be drawn integrally with different dies, the dies being changed for a narrower drawing after the larger diameter is drawn over a first portion. The two columns may be separately internally coated with different polarity materials for better separations.

Advantageously, the heaters for the first and second columns are electrically resistive conducting coats on the column exteriors. The resistivities of the conductive coats are selected in connection with the current to be applied to provide the appropriate temperature changes or rates of change. Resistivities may conveniently be changed by altering the thickness and/or composition of the resistive external coat on a column.

One or both columns may be temperature programmed by varying the potential applied across the conductive coats as a function of time. Moreover, the conductive coats have a different resistivity or gradients of resistivity to electrical current in different locations to provide either a continuous or substantially stepwise temperature gradient field spanning the region in which columns or capillary channels are located. The longitudinal axis of one or both columns may traverse the thermal gradient field in a direction substantially parallel to the thermal gradient field, inclined thereto, or at some places parallel and at others inclined.

In operation, a sample is injected into the first column through injector means communicating with the inlet end of the first column. Sample may be inserted into the injector means in solid or liquid form and vaporized before being carried by gas into the column. The sample may also be injected as a vapor or gas. Alternatively, a negative pressure may be applied across the columns such that a vapor or gas may be drawn into the columns. Such an arrangement, in combination with thermal modulation near the column inlet, could be used to sense an atmosphere in a room being tested for organic vapor contaminants, or for headspace analysis in a container, such as a container of ground coffee having vapors evaporating therefrom.

Under circumstances in which the sample is diluted in another gas or vapor, the sample may be collected against the cooler portions of the inlet of the first column for as long as necessary to achieve a given sensitivity, and then driven off in a sharper wave front for two-dimensional GC analysis.

In a comprehensive two-dimensional gas chromatograph, substantially all sample is collected in a series of bands, separated in time, but substantially non-overlapped at the outlet end of a first column. To permit comprehensive treatment of sample, the sample is driven off of the wall of the first column near its outlet end as a series of sharp sequential peaks into the second column, where further high speed gas chromatographic separation is performed at a fast enough rate to accomplish further resolution with minimum unplanned crossover of bands. Preferably, the sample is driven off by heat from the end of a first column, first modulator stage, then collected at the beginning portion of the second column, second modulator stage where the flow of carrier gas may be faster in some embodiments. The sample is then driven off as a sharp peak from the second modulator stage into the faster gas near the entrance end of the second column for further separation along the second column, and for detection or collection as bands at the outlet end of the second column.

From the above description, it can be understood that the apparatus and process of this invention has several advantages over prior art two-dimensional gas chromatography, such as for example: (1) it is small, compact and inexpensive; (2) it can sample very dilute vapors and gases so as to be usable to perform sampling in the atmosphere or in small containers; (3) it can provide a greater sensitivity and better resolution in a smaller size and in a shorter time because it can be subject to high speed temperature programming, thermal gradient operation and, gas flow rate programming; and (4) it can perform comprehensive two-dimensional separations, while achieving a substantially improved degree of independence or orthogonality between first and second retention times and substantially increased peak capacity per unit time as compared with a single column gas chromatograph, or prior art two-dimensional gas chromatographs.

BRIEF DESCRIPTION OF THE DRAWINGS

The above noted and other features of the invention will be better understood from the following detailed description when considered with reference to the accompanying drawings, in which:

FIG. 3 is a schematic drawing of an injector;

FIG. 4 is a simplified perspective view, partly broken away and exploded, of the chromatograph of FIG. 1;

FIG. 5 is another perspective view of the chromatographic system of FIG. 1, partly broken away;

DETAILED DESCRIPTION OF THE INVENTION

Operation of Comprehensive Two-Dimensional GC

Broadly, in this method, multiple second dimension chromatograms are generated during the first dimension chromatogram. The chromatographic data may be displayed in a three-dimensional manner with a retention parameter of the first column comprising one axis, a retention parameter of the second column comprising a second axis, and signal intensity comprising a third axis.

Figure 1:
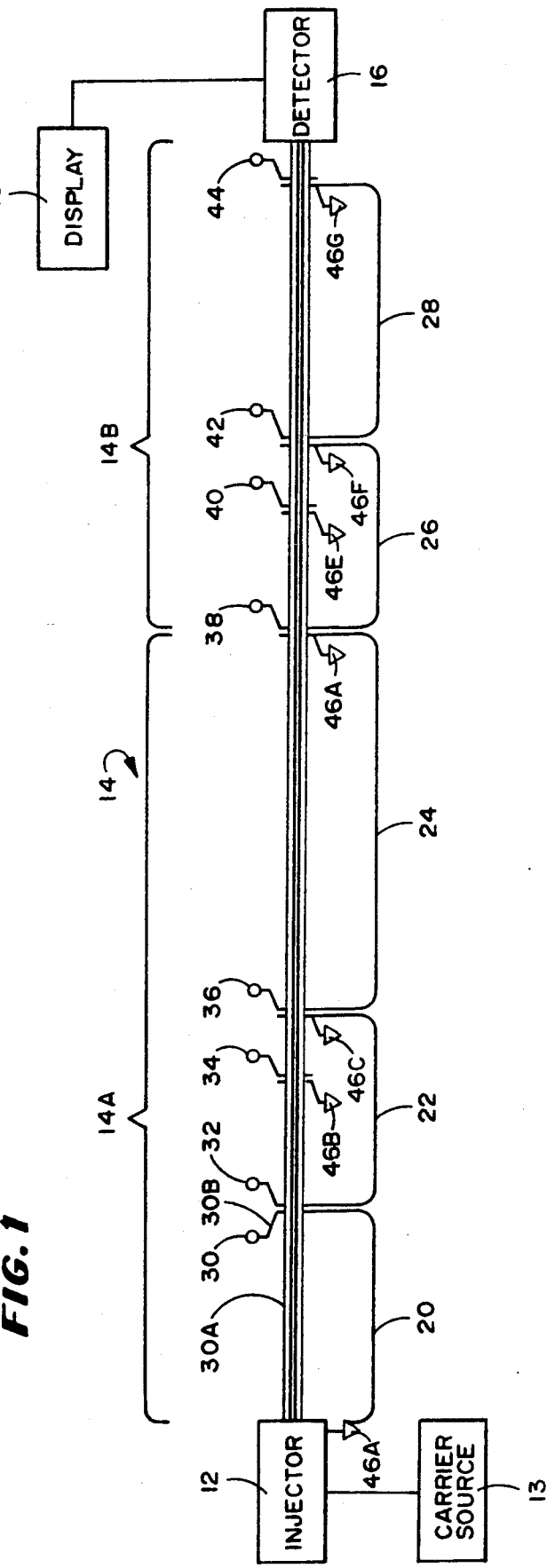
FIG. 1 is a block diagram of a chromatograph in accordance with the invention.

With reference to FIG. 1, there is shown a block diagram of a gas chromatographic system 10 having a sample injector 12, a source of carrier gas 13, a column system 14, a detector 16 and a display 18. The chromatographic column system 14 includes two sections 14A and 14B connected in series so that the inlet end of section 14B communicates with the outlet end of section 14A to receive carrier gas and sample therefrom. The sections 14A and 14B may be considered two columns that receive the same sample and carrier in series and as part of the same chromatographic run.

The column system 14 includes, in one embodiment, a transfer line 20, a first two-stage thermal modulator 22, a first chromatographic column 24, a second two-stage thermal modulator 26 and a second chromatographic column 28. The transfer line 20, first two-stage thermal modulator 22 and first column 24 are part of the first section 14A. The second two-stage thermal modulator 26 and second column 28 are part of the second section 14B.

To function as a chromatograph, the injector 12 receives sample and communicates with the carrier source 13 and the inlet port of the column system 14 to inject sample for movement along section 14A by the carrier source 13 at a first velocity. The sample then flows through section 14B, preferably, but not necessarily, at a faster velocity toward the detector 16. The detector 16 detects bands and displays separated peaks of the sample on a screen, printout or the like. The second section 14B has a shorter retention time than the first section 14A.

For some samples, a polar internal coat retains sample longer than a nonpolar internal coat. Thus, in some embodiments, the first section 14A has a nonpolar internal coat and the second section 14B has a polar internal coat so that the first section 14A separates principally by Van der Waals forces and the second column 14B by both Van der Waals forces and by dipole, induced dipole, hydrogen bonding or other forces between sample and the internal coat of the column.

The injector 12, carrier source 13, detector 16 and display 18 may be conventional and of a type well known in the art. The chromatographic system 10 is sufficiently sensitive so that the injector 12 can be merely a carrier-gas driven opening to collect very dilute sample from the atmosphere, from the headspace of closed containers through which the gas is moved, or the like, and yet obtain results. Thus, the system is capable of detecting alcohol vapor in an automobile or detecting drugs or the like from urine by drawing into its input, vapors from the automobile or vapors emitted from liquid in a container.

The different retention times between the first and second sections 14A and 14B are controlled by a number of factors, singly or in combination, such as: (1) the types of stationary phases in the two sections, (2) the volume per unit length of each column since the volume per unit length affects the carrier gas velocity, (3) the rate at which each section is temperature programmed; and (4) the presence of spatial negative thermal gradient fields traversed by the column section.

For some samples, a polar coat increases retention time more than a nonpolar coat. Thus, in some embodiments, the first section 14A has a nonpolar internal coat and the second section 14B has a polar internal coat so that the first section 14A separates principally by Van der Waals forces and the second column 14B by both Van der Waals forces and by dipole, induced dipole, hydrogen bonding or other forces between sample and the internal coat of the column.

One measure that makes the second section fast is to make the second column short, such as 10 cm (centimeters) to 200 cm in length. To achieve significant resolution with such a short column, a sharp concentration front, a sharp concentration pulse, or a series of sharp fronts and pulses should be admitted to the inlet of the short column. The time interval during which such sharp fronts or pulses are admitted must be accurately known in order to establish a time base on which to measure retention times of compounds eluting from a short second column into a detector located near the column outlet. Sharp concentration pulses or fronts will hereinafter be referred to as "wave fronts", since, by well known methods of Fourier decomposition, wave fronts or pulses may be viewed as superpositions of concentration waves, concentration distributions, or both.

Although two sections 14A and 14B in the chromatographic column system 14 are shown in FIG. 1, any number of sections may be utilized with significant improvement in sensitivity and resolution. The two sections may be formed integrally or formed separately and then connected with a butt joint. The absence of diversion valving between the first and second sections in the embodiment of FIG. 1 means all effluent from the first section traverses the second.

The transfer line 20 in FIG. 1 receives carrier gas and sample from the injector 12 with which it communicates and permits the gas and sample to flow into the inlet of the first two-stage thermal modulator 22. The inlet of the first two-stage thermal modulator 22 communicates with the outlet of the transfer line 20 and receives sample therefrom, causing sample to be collected against the wall of the first stage of the two-stage modulator. Periodically, the collected sample is ejected in a sharp wave front into the second stage of the first two-stage thermal modulator 22 where it is collected again and periodically ejected, preferably, but not necessarily, at a faster rate and within shorter time periods into the first column 24. For this purpose, the outlet of the first two-stage thermal modulator 22 communicates with the inlet of the column 24.

In the preferred embodiment, the heating means for certain columns, modulators, and transfer lines is a resistive conductive coat, or resistive coat upon an appropriate length of capillary column. The column is arranged to be electrically connected to an individual source of potential so as to individually heat the separated and insulated coats on the transfer lines, thermal modulator stages, or columns. The resistive coat may be part of a commercially available column of the type having conductive walls or outer sheaths, such as known aluminum-clad fused silica capillary columns, preferably, but not necessarily, with electrical isolation between conductive segments.

The terms "resistive coat" or "resistive-conductive coat," or in some contexts "conductive coat," in this specification means a coat or conductive cladding on a transfer line, thermal modulator or chromatographic column which coat or cladding is sufficiently conductive to permit the flow of electric current through the coat or cladding at voltages that are not damaging to a transfer line, thermal modulator, chromatographic column or other significant parts of a chromatographic system. The coat or cladding as defined is also resistive enough to generate heat at a rate capable of increasing the temperature of the transfer line, thermal modulator or chromatographic column at least 20 degrees Celsius per minute.

A thin gold layer positioned in place has been used in the preferred embodiment of the two-stage modulator as a resistive coat. The resistance of this coat is in the range of 10 ohms per centimeter of column length to 199 ohms per centimeter of column length and is preferably 50. Generally, the voltage selected for heating is no higher than 240 volts A.C. and no lower than one volt D.C. In the preferred embodiment, a low D.C. voltage such as 40 volts is used. Generally, commercially available aluminum-clad fused silica open tubular capillary tubes may be used such as those sold by SGE of Ringwood, Australia, and, Quadrex Corporation, New Haven, Conn.

Generally, the terms "conductive traces" or "conductors" as applied to connections between the columns and electrical components or between electrical components refers to ordinary printed circuit conductors of the lowest resistance that is cost effective since their purpose is principally the transmission of voltage rather than heating. Under some circumstances, a "resistive trace" may be used to combine the effects of heating and making an electrical connection. This may be used to match the temperature of electrical connections to the temperature of the column to avoid local or spot cooling of the column by heat transfer to wire leads or conductive traces.

Structure of the Transfer Line

The transfer line 20 and the rest of first section 14A are formed from a single open tubular capillary although separate tubes could be used. The transfer line 20 is internally coated, usually with a polar or a nonpolar substance, or its interior surface is deactivated. The line is arranged or positioned with a heating means on the outside that is separately controlled and at least partly physically separated from heaters for the first two-stage thermal modulator 22 and the first column 24.

The transfer line 20 includes a conductor 30 electrically connected to its resistive coat 30A by a resistive trace 30B. The coat extends substantially over the entire length of the transfer line although it is possible for it to extend over a shorter length. The coat is grounded near the injector 12 or within the injector at 46A but is electrically connected to the source of potential at its end adjacent to the first two-stage thermal modulator 22 through the resistive trace 30B and conductor 30. However, these connections could be reversed since their purpose is to control the temperature of the transfer line.

Structure of A Two-Stage Thermal Modulator

One component of this system generates concentration pulses in a gas stream flowing through a tube. The component consists of a length of tubing in which some substances carried with the gas stream are retained for a period of time and then released as a concentration pulse compact in distance and short in duration. This is accomplished with a mechanism whereby a first portion of the length of tubing accumulates retained substances at a relatively low temperature and releases them to a second portion of the length of tubing. The substances are released as a concentration pulse, compact in distance, upon application of heat. The second portion of the tubing holds the compact concentration pulse while the first portion cools sufficiently to again retain substances. Upon application of heat the second portion accelerates the compact concentration pulse so that it moves rapidly and becomes short in duration.

The first portion of the length of tubing may alternatively contain more than one stage for substance accumulation and concentration pulse compaction. The length of tubing may contain an adsorbent stationary phase in its interior and an electrically conductive layer on its exterior. Alternatively, the exterior wall may be electrically conductive.

In accordance with the foregoing description, the first two-stage modulator 22 includes two separated heaters, each with its own ground connection and each insulated from the other. In the embodiment of FIG. 1, these two heaters are conductive resistive coats on the exterior wall of the capillary column system 14, each coat being electrically connected by a resistive trace to a controlled source of potential, at one end, and grounded by another resistive trace at the other end enable modulation of their temperatures. The first coat is electrically connected at 32 and grounded at 46B and the second is electrically connected at 34 and grounded at 46C. The first coat and electrical contact are adjacent to, or preferably overlapping (but insulated from) the transfer line 20, and the second coat and electrical conductor are adjacent to, or preferably overlapping (but insulated from) the first column 24. Hereinafter, such a combination of heaters will be referred to as a "two-stage on-column thermal modulator", a "two-stage modulator", a "thermal modulator", or simply a "modulator". The first heated portion of the two-stage modulator will be referred to as the "first stage". The second heated portion of the two-stage modulator will be referred to as the "second stage".

Single-stage, two-stage, or multi-stage thermal modulators, in addition to providing sharp wave fronts between first and second sections of a comprehensive two-dimensional gas chromatograph, may be advantageously employed elsewhere in the chromatographic system. For example, an on-column thermal modulator can be used to form periodic, or repetitive, sharp concentration pulses or fronts at the beginning of the first column. Thus, it is possible to modulate a continuous incoming sample stream, as in a headspace analysis, or to preconcentrate a sample pulse from a conventional injector communicating with the first column to improve resolution of the first column.

Operations of Two-Stage Thermal Modulators

With this arrangement, the first stage of the thermal modulator including conductor 32 and ground connection 46B is cooled to collect sample that is flowing from the transfer line 20 through its interior. Following an appropriate collection period, the first stage of the two-stage thermal modulator is heated while the second stage, controlled by conductor 34 and ground connection 46C, is cooled so that a sharp wave front is generated in the first stage and transmitted to the second stage where, because the second stage is cooler, the wave front collects on the interior of the second stage. Then, the first stage is cooled and the second stage heated so that the second stage drives off the sample in a sharp wave front (concentrated sample) into the first column 24 while sample is again collected in the first stage.

With this arrangement and time sequence, a sample component as a relatively dilute vapor or gas can be received from the injector 12 such as from the atmosphere of a room or the like for a long sampling time and yet be sufficiently concentrated to provide sufficient chromatographic resolution (narrow injection bandwidth) and sensitivity to identify the components in the sample. On the other hand, the transfer line 20 and first two-stage thermal modulator 22 may be omitted so that the injector 12 may apply sample and carrier gas directly to the first column 24. Alternatively, additional stages of modulation are provided for greater focusing effect, or collection of large samples.

In one mode of operation, the second modulator stage concentrates bands or portions of bands from the first modulator stage into narrow peaks to increase resolution and sensitivity obtained with the next chromatographic column. In this mode, the first and second stages are heated sequentially by synchronized electrical current pulses. The first stage collects retained substances over a relatively long time from a relatively large volume of carrier fluid. It is preferred to accumulate one or a fraction of one entire band and not parts of two bands. Alternatively, groups of bands may be accumulated if desired. It is useful to chop a single band into a multiplicity of "slices", all of which are analyzed in a second, high speed, chromatographic dimension.

In the embodiment depicted in FIG. 1, a current pulse is applied to the first modulator stage of the modulator 22 to release retained substances into the carrier fluid allowing them to flow onto the second stage of the modulator 22. The second stage, which is relatively cold at the moment of injection, focuses the concentration pulse into a small volume and holds it while the first stage cools enough to begin collecting substances again. Current pulses applied to the second stage raise the temperature of the stationary phase so that the concentration pulse moves into the chromatographic column 24. In the preferred embodiment the second stage is heated by a sharp current pulse to increase the temperature of the necessary thermal mass thereof so as to vaporize held sample, or cause desorption thereof. Then the current pulse is lowered, held, or controlled to maintain a constant programmed temperature.

The second modulator stage of section 14A is heated sufficiently so that the concentration pulse is completely released and travels at substantially the carrier fluid velocity by the time it reaches the end of the modulator stage and is near the inlet of column 24.

This mode of operation may be used to concentrate sample between the transfer tube 20 (FIG. 1) and the first column 24 by using the first two-stage modulator 22 (FIG. 1) or to supply sample to another instrument, such as a mass spectrometer at the end of the last section, if a modulator is positioned near the outlet of the column system 14.

The sample peaks may have a band width of between 10 and 100 milliseconds and a volume of 5 to 100 picoliters. The second column must be fast enough to resolve the components of a peak driven from the second stage of its introductory modulator before another peak or portion of a peak is driven from the second stage of its introductory modulator into the second column.

Alternatively, a thermal modulator may be used to modulate the output stream of a gas chromatographic column used alone in a conventional gas chromatograph or the second column of a two-dimensional gas chromatograph so as to synchronize arrival of sample concentration pulses with pulsed, or synchronous detectors such as fourier transform, ion-trap, or time-of-flight mass spectrometers. The use of pulsed integrators, phase-locked loops, or the like may require such synchronization. On column thermal modulators may be used in combination at the inlet of the first column, near the junction of a first and second column, and possibly near the outlet of the second column of a two-dimensional gas chromatograph.

Comprehensive Two-Dimensional GC Column Structure

Structurally, the gas chromatograph of the present invention contains one or more of: (1) two serially connected and chemically distinct stationary phases such that the second stationary phase generates multiple chromatograms of the various sample substances emerging from the first stationary phase during the period of the chromatogram of the first stationary phase; (2) one column containing two chemically distinct stationary phases deposited serially in the column; or (3) one column containing one chemically uniform stationary phase but constructed such that a second portion of this column generates multiple chromatograms of the various sample substances emerging from the first portion of this column during the period of the chromatogram of the first portion of this column. A difference in retention mechanisms between the two portions of the column is due to a difference in the environment of the two portions of the one column. The difference in environment may be due to a difference in temperature, a difference in temperature program rate, a difference in intensity or wavelength of applied electromagnetic radiation, or a combination of these.

In this structure, the sample substances emerging from the first dimension of chromatographic separation are submitted to the second dimension of chromatographic separation. Substantially all of the sample quantity of each substance is submitted to the second dimension for chromatographic separation. The sample substances emerging from the first dimension of chromatographic separation may be input to the second dimension of chromatographic separation by a two-stage on-column thermal modulator. Sample substances may be input to the first dimension of chromatographic separation by a two-stage on-column thermal modulator.

A retention gradient in distance may be applied along either or both of the two stationary phases of the two-dimensional gas chromatograph. The retention gradient in distance is created by a temperature gradient or by a gradient in film thickness of the stationary phase or phases.

An additional detector may be placed near the junction between the two dimensions of chromatographic separation. The additional detector should be nondestructive and should allow the sample substances to flow through to the second dimension of chromatographic separation. Alternatively, the second detector may be destructive of the sample and be applied to a stream split off from the sample stream entering the second dimension of chromatographic separation. The signal from the additional detector is used to help determine the timing of modulation pulses applied to the second dimension of chromatographic separation. The additional detector may instead be placed part way into the second dimension of chromatographic separation such that the signal from this detector is used to adjust column temperature or flow rate to maximize the orthogonality of the two-dimensional chromatogram.

If the two dimensions of chromatographic separation are of comparable speed, a two-dimensional chromatogram is computed by deconvolving the response of the system to a pair of orthogonal modulation signals which were applied to the sample streams at or near the head of each dimension of chromatographic separation.

In constructing the first and second sections of the column system, a first method may be employed wherein they may be drawn separately, each to a different diameter, then connected with a butt connection having a tube or sealing ferrule over the abutted ends. In a second method, they may be drawn as one continuous tube having different size inner diameters in the first and second column or sections. The variation of diameters is effected through variation of drawing velocity or drawing a portion of a first column or section through a heated, but narrower die in a separate drawing step, to create a second column of smaller diameter than the first, or vice versa. A third method involves forming the two columns or sections in a continuous tube of constant diameter by coating the interior of a second column with a stationary phase different from that of the first, such that no gap exists on the tube interior, particularly in the region of transition from the first stationary phase to the second. In a fourth method the two columns may be formed from a single continuous capillary tube having only one type of stationary phase coated onto its inner surface by affixing an on-column modulator, which may be single or multi-stage, to the capillary exterior. The modulator defines the end of the first column and the beginning of the second. In a fifth method separate columns may be connected together in a "reverse open split" connection which provides for addition of carrier gas to the stream eluting from the first column, and substantially loss-free transmission of sample, together with additional carrier gas, from the first column to the second.

In the first, second and fifth embodiments described, carrier gas velocity in the second column may be made faster than carrier gas velocity in the first column. In the third and fourth embodiments, carrier gas velocity is the same in both columns. Other measures singly or in combination, such as the use of a short second column, or the imposition of axial negative thermal gradients combined with temporal temperature programming, may be used to increase the rate of separation of sample in the second column.

Temperature Control Means

First and second columns of the two-dimensional gas chromatograph may be placed together in a single oven, which may be temperature programmed, or separate ovens, which may be independently temperature programmed. However, alternative means of heating the first and second columns could include: (1) powered resistive conducting coatings on the column exterior; (2) external heaters in thermal contact with a thin support on which the capillary columns are mounted; (3) external heaters in thermal contact with a wafer structure in which the capillary channels are embedded; (4) heat exchange means between the capillary mounting structure and an external heater; or (5) thermal gradient means applied to one or both columns, which, in combination with appropriate temperature programs, may exert advantageous focusing effects which may be used to increase the speed of one or both columns or capillary channels. Again with reference to FIG. 1, first column 24 includes a single heatable coat under the control of a single conductor 36 and ground 46D. However, multiple segments may be used to provide further thermal programming, if desired. Moreover, the resistivity may change along its length to provide a temperature gradient such as, for example, by changing the thickness or composition of a conductive coat along the column length. With this arrangement, the temperature may be increased or decreased within the column to program the temperature with respect to time and also to establish a different spatial (longitudinal) temperature or gradient of temperature, with respect to prior sections and subsequent sections.

To further resolve the components of the sample, the second section 14B has a shorter retention time, is usually smaller in diameter, shorter, and commonly has a different interior coat, but may have the same coat. Preferably, the retention time range of the second section 14B should be one third to one fifth, or less, of the band duration (peak width) of the first section 14A, but may also be as long as or several times longer than the band duration (peak width) of the first section 14A. The second section 14B includes temperature controllable external coats on the second two-stage thermal modulator 26 and second column. The latter coat may or may not provide temperature gradient control on the shorter second column 28, although, instead of resistant coats on capillary columns, separate external heaters or ovens each controlling a portion of column at a different temperature could be used to provide temperature gradient control or to heat portions of a column.

The second two-stage modulator 26 receives sample at its inlet from the outlet of first column 24 and transmits sample from its outlet to the second column 28. The first stage of the two-stage thermal modulator 26 has one end in communication with the outlet of the first column 24 and is first dropped to a temperature cooler than that of the first column 24 to receive sample which is laid down upon the interior surface of the modulator.

The temperature of the first stage of the second thermal modulator is controlled by a conductor 38 grounded at 46E to lower the temperature below that of the first column 24 by lowering or disconnecting the potential while the first column 24 is heated. Thus, sample collects on the interior surface of the first stage of the two-stage thermal modulator. The temperature of the first stage may then be increased to drive the sample off as a sharp wave front onto the second stage, which is temperature controlled by a resistive coat heater energized by an electric potential connected across it through a conductor 40 and the ground 46F to heat that section of the column by Julian heat from its resistive coat. The temperature of the second stage is dropped shortly before the front from the first stage enters to collect a sample in the second stage and then is increased to drive off the portion of the sample so collected as a sharp wave front into the second column 28 for further resolving in the second column 28.

The voltage used for heating is approximately 40 volt d.c. in the preferred embodiment, and the temperature can be controlled in accordance with the separation that is being performed. Generally, two stages of modulation are sufficient but any number can be used with successive modulator stages further sharpening the pulses. They operate by accumulating sample for a time period on a cooled section which band is thereby heating the section to drive off a wave front of the sample as a narrower peak. Usually, the timing is controlled to accumulate a portion of a band from a slower column and then concentrated for transmission through a faster column having a shorter retention time.

The second column 28 has its temperature controlled by a conductor 42 grounded at the opposite end of its coat at 46G. While one current is shown being applied to one coat for the second column 28, multiple coats and multiple electrical conductors could be used to provide further time and temperature programming, thermal steps, or thermal gradients, if desired.

Conductor 44 is used to heat a short length of tubing connecting the outlet of column 28 to detector 16. The ground is not shown.

It is possible with some nondestructive detectors, such as heat of adsorption or absorption detectors, light absorbance detectors, thermoconductivity detectors or the like, to detect sample nondestructively between sections. It is also possible to capture as much of a band as possible before injecting it into the second column to maximize sensitivity. Programmed voltage signals may provide time and temperature programming under the control of pulse sequences stored in a microprocessor to optimize conditions. These techniques may be used with very small or dilute samples since concentrating the sample band by a series of modulations from cold to hot and back to cold provides sharp sample bands and therefore sufficient resolution on the second column, with or without thermal gradient programming along the column.

Comprehensive Three-Dimensional GC Structure

Figure 2:
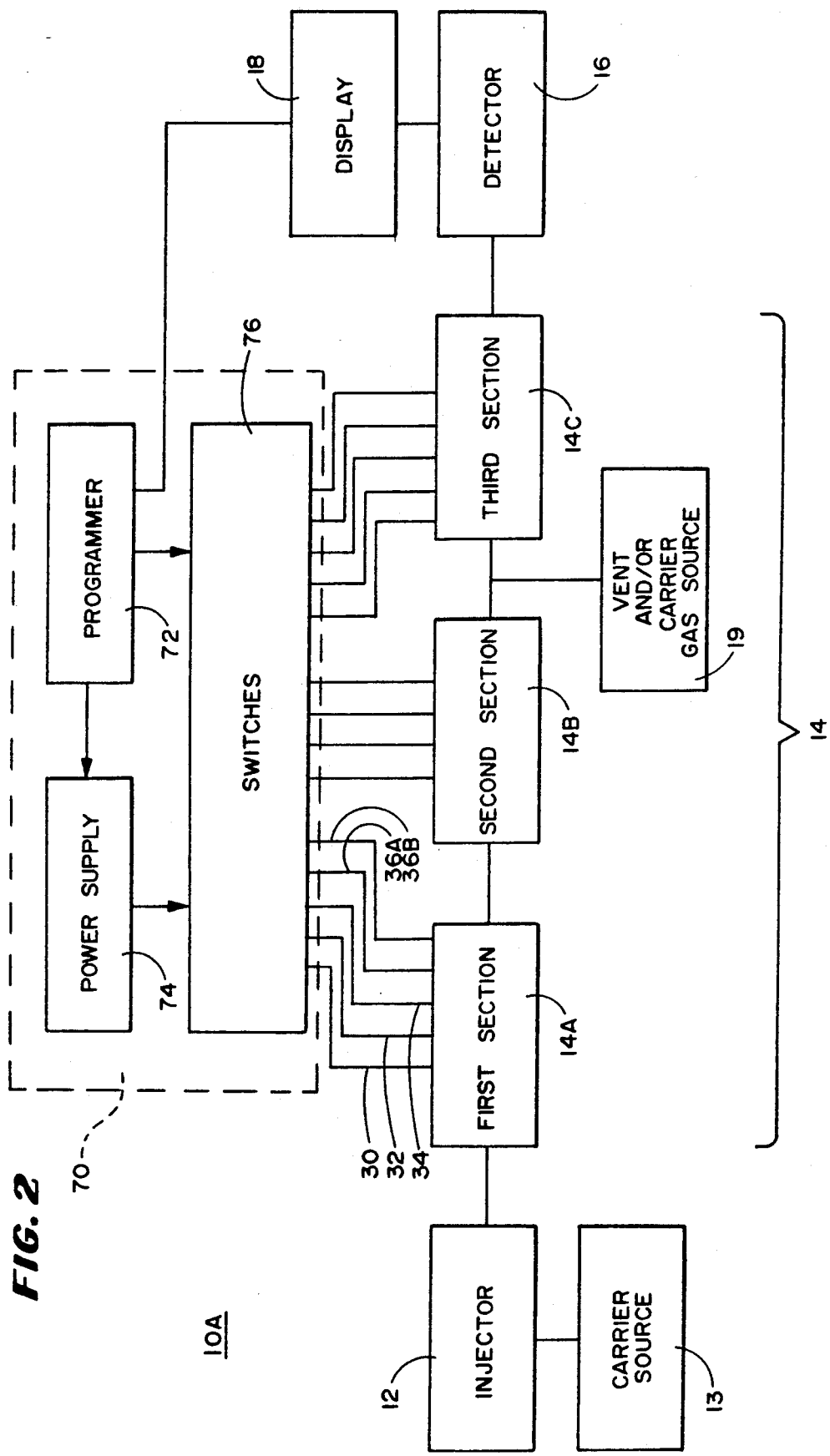
FIG. 2 is a block diagram of a three-dimensional gas chromatograph according to the present invention.

In FIG. 2, there is shown a block diagram of an embodiment 10A of a chromatograph having an injector 12, a source of gas 13, a column system 14, a detector 16, a display 18, a vent 19 and a programmable microcomputer controlled arrangement 70 for controlling the programming of the column system 14. In the embodiment of FIG. 2, the carrier source 13, injector 12, column system 14, detector 16 and display 18 are similar to that of FIG. 1 and connected as shown. However, the column system 14 is shown as including 3 sections of columns, each with successively shorter retention times at 14A, 14B and 14C. All of the arrangements are electrically connected through a microprocessor system 70 which controls the application of heating potential to the different electrodes and different sections of the column system 14 to provide comprehensive three-dimensional gas chromatography.

The microprocessor system 70 includes a programmer 72, a power supply 74 and a plurality of switches and drivers 76. The switches and drivers 76 are electrically connected to the conductors in the first section 14A, second section 14B and third section 14C, which conductors are numbered the same as in FIG. 1 except that there are a plurality of additional coats and conductors like those indicated at 36A, 36B and the like, for the second section 14B. There could also be further modulator stages to provide three-stage or four-stage modulators and the like.

With these arrangements, the programmer 72 opens and closes the switches or controls drivers 76 to apply power to the coats. Pre-programmed runs may be made and the temperatures may be determined by running samples through the system and measuring the results so that the system can be rated and electrical potentials and times of application established to reach certain temperatures. Also timed runs can be made to resolve entire bands of a sample if desired by running them through the system and correlating the display results with the programmer 72 to obtain the proper values for heating and the proper times for accumulating and driving off signals that give the greatest sensitivity, greatest resolution and greatest peak capacity.

Under some circumstances, the velocity of the carrier-gas can be adjusted with benefit to resolution or sensitivity. For this purpose, two sections may have a vent carrier gas source 19 separating them, which vent can be opened to supply additional carrier gas to the third section and thus increase the linear velocity of the carrier gas through the section 14C. Alternatively, some carrier gas may be vented or exhausted, if desired, to reduce carrier velocity in the next section.

The chromatograph can beneficially be optimized to detect a specific ingredient, such as cocaine in a sample of urine or alcohol in the atmosphere of an automobile. In constructing a column for this purpose, the designer knows ahead of time the normal ingredients in the sample of urine or the atmosphere in an automobile and the characteristics of the substance that the designer wishes to detect. With that in mind, a number of conditions or sections may be selected for optimum performance.

At the factory, the temperatures of the column can be measured using known samples and this can be correlated within the programmer memory with times and potentials to remove the need for measuring the temperature of the coats and correlating them with the temperature of the column for future use. Of course, in addition to the use of known samples to obtain data on temperature changes, temperature sensitive sensors may be used or changes in the resistivity of the resistive coat may be used to determine temperature.

The Use of Thermal Gradients

Returning to FIG. 1 and resolution can be improved along the column 28 under some circumstances by creating, establishing and/or controlling a thermal gradient along the column. Preferably, the spatial thermal gradient is negative and is programmed in time along the column. The temperature along the column is controlled to create a multiplicity of moving characteristic temperature zones. In this description, the term "characteristic temperature" means the temperature at which the thermal focusing effect associated with a negative thermal gradient substantially balances band broadening of a component. For example, with the temperature decreasing toward the outlet end of the column 28, chromatographic bands are compressed as the rear of each band moves faster than the front until compression balances broadening of a band.

A wide variety of gradients can be obtained by the following steps or from combination of the following steps: (1) transmitting the current through a resistive coat, particularly if the current is varied to generate a temperature gradient in time and the resistance graded in the coat to vary heat generation along the axis of the column; (2) the pitch of wound loops of column is varied to vary heat transmission from one portion of the winding to another; (3) a flow of gas is directed longitudinally over a looped column to transport heat from the outlet end to the inlet; and (4) several insulated sections of resistive coat are independently heated in a spatial and/or temporal programmed sequence.

The two gradients, which are changes in temperature at fixed locations as time passes and temperature changes along the longitudinal axis of the column at any one time, together create a moving temperature profile. In some configurations, a particular temperature propagates down the column at a rate determined by the ratio of the two gradients. Each substance in the sample to be separated focuses at a particular temperature determined by the substance's chemical equilibrium constant of interaction with the stationary phase, by the ratio of the two gradients (which ratio may vary with distance travelled along the column), and by the carrier gas linear velocity along the column. The moving temperature profile then carries each substance along the column to the detector 16 at the end of the system 14.

In such a design, the first section 14A is selected to have time, temperature and spatial gradients that normally cause a band containing the component being investigated to be moved rapidly to the end of the first section 14A, where it is concentrated into a narrow wave front for preferably faster movement down the second section 14B, which section 14B may have a different stationary phase chemistry to further separate the component. The second section 14B is designed to move sample bands as rapidly as possible to the end with further separation. The band may be subjected to further steps of concentration and separation as in a third section 14C to use the shortest possible time and obtain the greatest sensitivity and resolution for a peak indicative of the compound being investigated and generally its amount.

Generally, in performing gas chromatographic analysis of a sample from an inlet port of the section 14A to a downstream portion at an elution port, a temperature control means is provided in thermal transfer relationship with the column 24, which temperature control means is adapted to heat or to cool selected locations of the column 24. A stepwise, piecewise, continuous, curvilinear-shaped, linear-shaped negative temperature gradient positive temperature gradient or combination thereof, may be provided along the column 24 as well as any temporal variations thereof by the temperature control. Preferably, the heat is applied by contact electrical heating means.

The temperature at the elution port of the column 14 may be maintained lower than the temperature at the inlet port at all times during the analysis so that the sample can continuously be subjected to a lower temperature as it travels in a downstream direction along the column 14 or to any other temperature gradient.

The temperature at the elution port may, however, be increased at the end of the analysis. The temperature control means is capable of transferring changes of at least about 0.5 degrees Celsius per second to the column 14. The temperature of the column 14 may be raised at the elution port at the end of analysis so that the sample will elute from the column 14, may be maintained hot while the rest of the system is thermally reset, or may itself be thermally reset.

Although in one embodiment, the gradient is obtained by controlling heat transfer between loops of a helically wound column or by separately heating different loops, it may be obtained from a coolant gas introduced near one end of the helix, such as by a nozzle 117 (FIG. 4) and withdrawn at another nozzle such as 119 (FIG. 4) so that it passes over the column 14 (FIG. 5). This fluid may be at any temperature such as room temperature, and for some uses should be less than about 100 degrees Celsius. When operated in that mode with open tubular chromatographic columns, the downstream ends of the column are maintained at a lower temperature than the upstream portion during all but the end point of the analysis. This mechanism may be used to provide a negative thermal gradient under the control of a temperature control programmer.

To optimize performance, any of several factors can be controlled. These are selected to obtain the best combination of time of analysis, resolution and sensitivity. However, the length of each column is selected to focus the components being investigated and time and temperature programming are designed for a favorable "capacity factor" as described below.

Theory of Thermal Gradient Gas Chromatography

A chromatographic band broadens as it moves down the column. The amount of broadening is primarily determined by the distance moved according to equation 1 where sigma is the band standard deviation, x is the distance moved down the column, and H is the column plate height. H is assumed to be independent of time and position along the column. The variance of a band increases in direct proportion to the distance moved, as shown by equation 2.

The rate of increase in variance with respect to time is found by taking the derivative of this expression. The derivative, dx/dt, is the band velocity, $u_s$. The velocity of a band is related to gas velocity, u, and the partition of coefficient k, and the relationship between them is shown by equation 4.

In addition to the above band spreading effect, there is a focusing effect caused by the temperature gradient along the column. If the temperature decreases with distance along the column, then the rear of the chromatographic band is at a higher temperature than the head of the band and so moves at a higher velocity. The rear tends to overtake the front of the band, causing focusing. If, over the width of a band, the temperature gradient is of approximately constant slope, the rate of focusing is directly proportional to the velocity gradient along the column because a larger gradient produces a greater difference in band velocity as shown by equation 5. Consequently, an increase in velocity can focus bands and thus can improve separation. Downstream stages of a multiple dimension chromatographic system may benefit from narrower diameter resulting in greater carrier gas velocity, or added carrier gas. To find how the variance changes with time due to this focusing effect, the derivative of the variance is taken with respect to time and then substituted, resulting in equation 6 and equation 7.

The chromatographic band should reach a point at which the rates of focusing and broadening are balanced and the band variance is constant as shown in equation 8. Substituting the rates of spreading and focusing into this equation gives equation 9. Solving for the variance of the focused band gives equation 10.

The variance depends on the gradient of the capacity factor along the column. The capacity factor gradient is related to the temperature gradient through the definition in equation 11 where K is the equilibrium constant and delta H is a $$\sigma = \sqrt{Hx} \qquad \text{Equation 1}$$

$$\sigma^2 = Hx \qquad \text{Equation 2}$$

$$\frac{d\sigma^2}{dt} = \frac{d(Hx)}{dt} = H\frac{dx}{dt} = Hu_s = \frac{Hu}{(k+1)} \qquad \text{Equation 3}$$

$$u_s = u/(k+1) \qquad \text{Equation 4}$$

$$\frac{d\sigma}{dt} = \sigma\frac{du_s}{dx} \qquad \text{Equation 5}$$

thermodynamic heat of interaction with the stationary phase. The constant, beta, is the phase ratio and the constant, a, is related to the entropy of solution through ln a = delta S/R where delta S is the change in entropy of interaction with respect to temperature T, and R is the gas constant.

Taking the derivative of the capacity factor with respect to column distances gives equation 12, equation 13 and equation 14. Substituting this into the equation for the variance of the focused band gives equation 15. For simplicity, assume that the temperature gradient is linear with distance along the column. Then the temperature gradient is the difference in temperature from beginning to end of the column divided by the column length in equation 16. Substituting and rearranging gives an expression for the focused variance in equation 17 and equation 18. The duration of a chromatographic band, sigma t, as it elutes from a column is equal to its length, sigma, divided by its velocity, u/(k+1). Taking the square root of the band variance and substituting it into this relationship gives equation 19. Equation 19 can be rearranged into equation 20.

$$\frac{d\sigma^2}{dt} = 2\sigma\frac{d\sigma}{dt} = 2\sigma^2\frac{du_s}{dx} \qquad \text{Equation 6}$$

$$\frac{d\sigma^2}{dt} = 2\sigma^2 u \frac{d((k+1)^{-1})}{dx} = -2\sigma^2 u(k+1)^{-2}\frac{dk}{dx} \qquad \text{Equation 7}$$

$$\left(\frac{d\sigma^2}{dt}\right)_{spreading} + \left(\frac{d\sigma^2 j}{dt}\right)_{focussing} = 0 \qquad \text{Equation 8}$$

$$\frac{Hu}{(k+1)} - \frac{2\sigma^2 u}{(k+1)^2}\frac{dk}{dx} = 0 \qquad \text{Equation 9}$$

$$\sigma^2 = \frac{H}{2}\frac{(k+1)}{(dk/dx)} \qquad \text{Equation 10}$$

$$k = \frac{K}{\beta} = \frac{a}{\beta}e^{\Delta H/RT} \qquad \text{Equation 11}$$

$$\frac{dk}{dx} = \frac{a}{\beta}\frac{d(e^{\Delta H/RT})}{dx} = \frac{a}{\beta}e^{\Delta H/RT}\frac{d(\Delta H/RT)}{dx} \qquad \text{Equation 12}$$

-continued $$\frac{dk}{dx} = \frac{a}{\beta} \frac{\Delta H}{R} e^{\Delta H/RT} \frac{d(T^{-1})}{dx} =$$ Equation 13

$$-\frac{a}{\beta} \frac{\Delta H}{RT^2} e^{\Delta H/RT} \frac{dT}{dx} = -\frac{K}{\beta} \frac{\Delta H}{RT^2} \frac{dT}{dx}$$

$$\frac{dk}{dx} = k \frac{\Delta H}{R} \left( \frac{-dT/dx}{T^2} \right)$$ Equation 14

$$\sigma^2 = \frac{H}{2} \frac{(k+1)}{k} \frac{RT}{\Delta H} \left( \frac{T}{-dT/dx} \right)$$ Equation 15

The factor (k+1)/k is close to 1 at large capacity factors and might be eliminated from the above expression but is left in equation 20. This expression for band duration has a general form similar to that for conventional isothermal chromatography as shown in equation 21, except that the band duration is modified by the addition of a focusing factor dependent on the temperature gradient along the column and the equilibrium constant. With a large temperature gradient and low column temperature, the band duration may be much less than for an isothermal chromatogram.

Linear temperature gradients in both distance and time are defined by equation 22 and equation 23 where delta $T_x$ and delta $T_t$ are the temperature differences in distance and time, respectively, and L and D are the column length and chromatogram duration, respectively. By imposing temperature gradients in both time and distance, we create a moving temperature profile along the column. The characteristic velocity with which the temperature profile moves along the column is the ratio of the gradients in equation 24.

$$-dT/dx = \Delta T_x/L$$ Equation 16

$$\sigma^2 = \frac{H}{2} \frac{(k+1)}{k} \frac{RT}{\Delta H} (TL/\Delta T_x)$$ Equation 17

$$\sigma^2 = HL \frac{(k+1)}{k} \frac{RT}{2\Delta H} \frac{T}{\Delta T_x}$$ Equation 18

Equation 19

$$\sigma_t = \sigma \frac{(k+1)}{u} = \frac{(k+1)}{u} \sqrt{HL \frac{(k+1)}{k} \frac{RT}{2\Delta H} \frac{T}{\Delta T_x}}$$

Equation 20

$$\sigma_t = \sqrt{HL} \frac{(k+1)}{u} \sqrt{\frac{(k+1)}{k} \frac{RT}{2\Delta H} \frac{T}{\Delta T_x}}$$

Sample substances should move along the column at the characteristic velocity, assuming that it is not greater than the carrier gas velocity. If a substance happens to be far down the column, it is at a low temperature and so is moving slower than this velocity. Progressively higher temperatures overtake the substance raising its velocity until it matches the characteristic velocity of temperature propagation along the column. If a substance is behind this temperature, it is at a high temperature and so is moving faster than the characteristic velocity. It overtakes progressively lower temperatures reducing its velocity until it again matches the velocity of temperature propagation along the column.

Each substance eventually reaches a focus temperature (characteristic temperature) and then moves at characteristic velocity with that characteristic temperature along the column. The column must be sufficiently long for a sample substance to reach its focus temperature before it reaches the end of the column. Consequently, the choice of temperature gradient in designing the column is governed by the desire to select focus temperature and characteristic velocity such that $$\sigma_t = \sqrt{HL} \frac{(k+1)}{u}$$ Equation 21

$\Delta T_x/L$ = gradient in distance  Equation 22

$\Delta T_t/D$ = gradient in time  Equation 23

$$u_s = \frac{\Delta T_t/D}{\Delta T_x/L}$$ Equation 24

$$u_s = \frac{u}{(k_f + 1)}$$ Equation 25 the compound being investigated moves with the focus temperature zone at the highest possible velocity.

The velocity of chromatographic migration along a column is given by equation 25 where $k_f$ is the capacity factor of the substance at its focus temperature. Solving for the focus capacity factor and substituting the temperature propagation velocity gives equation 26 for the focus capacity factor.

Each substance should reach a focus at a temperature where its capacity factor is equal to the above quantity. This focus capacity factor depends only on parameters of the chromatographic system and is, therefore, independent of substance. More volatile substances focus at lower temperatures and so reach the end of the column sooner, but every substance moves at the same characteristic velocity at the same characteristic capacity factor given above. This result depends on the assumption that the focus temperature is within the range of the gradient and that sufficient time has elapsed to reach the focus temperature.

With a typical column length of 100 cm and a typical chromatogram duration of 2 seconds, the ratio L/D=50 cm/sec. If we assume that the two temperature differences, delta $T_x$ and delta $T_t$, are approximately equal and that a reasonable capacity factor, $k_f=5$, is desired, then a linear velocity u=250 cm/sec is required to satisfy equation 26. Consequently, exceptionally high carrier gas velocity is desirable to get good separation. At low velocities, column efficiency is low because $k_f$ is too small.

The characteristic capacity factor is related to temperature by equation 27 where $K_f$ is the characteristic equilibrium constant for the system and $T_f$ is the focus temperature for a particular substance. Taking a logarithm and rearranging gives an expression for the focus temperature in equation 28.

A particular substance has a focus temperature directly proportional to its heat of solution, H, in the stationary phase. This dependence of focus temperature on heat of solution is the source of separation in this thermal focus technique. Capacity factor is a constant of the system. Substituting the focus capacity factor, $k_f$, for k and the focus temperature $T_f$, for T gives equation 29.

Equation 26

$$k_f = \frac{u}{u_s} - 1 = u \left( \frac{\Delta T_x/L}{\Delta T_t/D} \right) - 1$$

-continued $$k_f = \frac{K_f}{\beta} = \frac{a}{\beta} e^{\Delta H/RT}$$ Equation 27

$$T_f = \frac{\Delta H}{R \ln(\beta k_f/a)}$$ Equation 28

Equation 29

$$\sigma_t = \sqrt{HL} \ \frac{(k_f+1)}{u} \ T_f \sqrt{\frac{(k_f+1)}{k_f} \ \frac{R}{2\Delta H \Delta T_x}}$$

$$R_s = \frac{\Delta t_r}{4\sigma_t}$$ Equation 30

Short band durations result from low operating temperature. A low operating temperature can be obtained by using a high carrier gas velocity to drive the sample substances further down the column or by delaying the beginning of the temperature gradient in time. Both of these effects have been experimentally observed. H may also be reduced by operating at lower temperature through its dependence on capacity factor through the Golay equation.

The next step is to find an expression for resolution starting from the definition in equation 30. The difference in retention times for a pair of substances, delta $T_r$, can be derived from the difference in focus temperature, delta $T_f$. Dividing by the temperature gradient along the column converts the difference in temperature into a distance along the column. Dividing the distance by velocity converts it into a difference in time in equation 31. The previously derived band duration is in equation 32. Substituting these into the resolution equation gives equation 33, equation 34 and equation 35. Substituting N = L/H gives equation 36.

The ratio of the difference in focus temperature to focus temperature can be reduced in equation 37 where delta H is the difference in heats of solution. Substituting into the resolution equation gives equation 38.

From these equations, it can be understood that capacity factor is an important reason why a temperature gradient along a column improves resolution over what can be obtained by conventional temperature programming. In conventional temperature programming, the capacity factor varies with time and is small near the end of the column. Small capacity factor increases H and decreases N through the Golay equation. Most of the column is traversed with small capacity factor. In this temperature gradient technique, however, the capacity factor is larger, especially at the end of the column.

Higher carrier gas linear velocity improves resolution by driving chromatographic bands further down the temperature gradient on the column. This increases the value of the focus capacity factor which both increases N through the Golay equation and directly increases resolution through the $$\Delta t_r = \left(\frac{\Delta T_f}{\Delta T_x/L}\right)/u_s = \frac{\Delta T_f}{\Delta T_x} L \frac{(k_f+1)}{u}$$ Equation 31

$$\sigma_t = \sqrt{HL} \ \frac{(k_f+1)}{u} \ T_f \sqrt{\frac{(k_f+1)}{k_f} \ \frac{R}{2\Delta H \Delta T_x}}$$ Equation 32

$$R_s = \frac{\frac{\Delta T_f}{\Delta T_x} L \frac{(k_f+1)}{u}}{4\sqrt{HL} \ \frac{(k_f+1)}{u} \ T_f \sqrt{\frac{(k_f+1)}{k_f} \ \frac{R}{2\Delta H \Delta T_x}}}$$ Equation 33

$$R_s = \frac{\Delta T_f}{T_f} \ \frac{L}{4\sqrt{HL}} \ \frac{1}{\Delta T_x} \sqrt{\frac{k_f}{(k_f+1)} \ \frac{2\Delta H \Delta T_x}{R}}$$ Equation 34

$$R_s = \frac{\Delta T_f}{T_f} \ \frac{L}{\sqrt{HL}} \sqrt{\frac{k_f}{(k_f+1)} \ \frac{\Delta H}{8\Delta T_x R}}$$ Equation 35

$$R_s = \sqrt{N} \ \frac{\Delta T_f}{T_f} \sqrt{\frac{k_f}{(k_f+1)} \ \frac{\Delta H}{8\Delta T_x R}}$$ Equation 36

$$\frac{\Delta T_f}{T_f} = \frac{\Delta \Delta H}{\Delta H}$$ Equation 37

$$R_s = \sqrt{N} \ \Delta\Delta H \sqrt{\frac{k_f}{(k_f+1)} \ \frac{1}{8\Delta T_x \Delta H R}}$$ Equation 38

$k_f/(k_f+1)$ factor. A gentle gradient is most effective (delta $t_x$), but more time is then required to reach focus temperature. A nonlinear gradient, under some circumstances, may be useful in maximizing resolution per unit time. A factor that may be significant with high carrier gas velocity is gas compressibility. However, short columns and/or the band focusing effect reduces band spreading due to gas expansion or diffusion along the column before a band reaches the end of the column.

Orthogonality of the Multi-Dimensional Gas Chromatograph

When separation of a multiplicity of peaks is maximized, or nearly maximized, with respect to some statistical measure of separation, the various sections of a comprehensive two or higher dimensional gas chromatograph are "orthogonal" or "nearly orthogonal" or "as orthogonal as is practical" or simply "tuned".

In one mode of operation, and in connection with making successive separations maximally independent and causing the experimental parameters to separate components in the later sections that were not sufficiently separated in earlier sections, it is preferred to maximize the orthogonality of the system for a given analysis. This means reducing to the greatest practical degree, the interdependence of or correlation between retention times or peak migration velocities between sections or to increase the difference in manner the experimental parameters affect the mobility of components which are unresolved in earlier sections. This way, such unresolved components move down successive sections at speeds differing from each other by more than such speeds differed in earlier sections.

Consider a two-dimensional GC experiment for simplicity (it being understood that similar principles can be applied to more than two chromatographic sections). It is possible, for example, to make the second dimension retention times or migration velocities of a known homologous series of compounds that elute in a predictable manner depend not at all or at most, only weakly, upon first dimension retention times. Thus, second dimension retention times or migration velocities do not vary with respect to first dimension retention times. An example of such a homologous series is a series of alkanes each differing from a lower mass alkane by one carbon atom. This condition occurs, for example, if the second dimension retention times of the members of a homologous series are made equal, even though they are well resolved on a first chromatographic dimension, i.e., their first dimension retention times are not equal.

These second retention times can be made equal by varying systematically in time certain experimental parameters of a second chromatographic section even as the first chromatographic section separates a sample into bands, as in, say, a conventional temperature programmed first chromatographic section. Experimental parameters of the second section that might be varied readily would include: (1) the temperature of the second column from one operational cycle to the next; (2) the carrier flow rate from one cycle to the next; and (3) the slope or curvature of a spatial thermal gradient from one cycle to the next. Other parameters could conceivably be varied, such as phase ratio, column volume or effective column volume, or the polarity of the stationary phase, provided these could be rapidly varied in a controlled manner.

More specifically, a column design is first selected that is suitable for the type of separation required. The tube has the appropriate lengths and modulators and internal coats to affect the mobility of the expected components that are to be investigated with the gas chromatograph. The second section of this column design is tuned operationally so that it does not materially change a known and completed resolution of a sample provided by the first dimension of the two-dimensional chromatographic column. This is considered one step in the process of rendering the retention times of the second section independent of the retention times of the first section.

A mixture containing members of the homologous paraffin series is injected into the inlet of the first section and is separated by the entire column. Then, with the experimental parameters of the first column adjusted so that the paraffins are not resolved and are eluted together, the experimental parameters of the second column are adjusted to provide even spacing between the paraffins of the homologous series.

This arrangement relies upon the chromatographer who does the tuning knowing ahead of time those conditions of the first section which do not resolve the series. Thus, he can be assured that when he accomplishes such resolution of the second series the even spacing is the result of experimental parameters in the second section and not the sum of two partial separations, one in each section. With the system so tuned, other paraffins should be affected differently by the two sections and thus components not separated in the first section should be separated in the second section.

In the case of a complex mixture analysis in which, for example, all or nearly all components are unknown at the outset, experimental conditions at the second column may be varied systematically from one cycle to the next so as to maximize some statistical measure of peak separation. To accomplish this, the unknown mixture is injected into the inlet of the first section. The peaks at the outlet of the second section are graphed, with the two-stage modulator operating, so that the peaks appear in the plane of a quadrant of a cartesian graph (retention plane) having first dimension retention time and second dimension retention time as axes. These times can be determined because the two-stage modulator establishes a time base at which the already modulated peaks are injected into the second column. Thus, the injection times are known for both sections of the column system and the elution times are approximately known from detector response.

The degree of variance from a correlation between the effects of the two sections is determined. Strong correlation is indicated by a diagonal straight curve on which the peaks all fall. Weak correlation is indicated by the failure of peaks to follow such a curve or any other regular curve such as commonly determined by a statistical determination of variance or correlation factor.

The experimental parameters in the two sections are then systematically varied from run to run empirically or using any of the techniques now used by chromatographers when attempting to increase resolution between successive runs of an unknown. However, in this situation, the chromatographer is attempting to minimize the correlation between the first and second retention times. For example, peaks falling on a diagonal straight line with small variance from the straight line indicate strong correlation between the two sections, whereas completely random location of peaks in the retention plane indicates weak correlation. Thus, the chromatographer attempts to space the peaks within the retention plane as evenly as possible rather than in a correlated fashion. The chromatographer varies the experimental parameters until he achieves this result to an acceptable degree and then the two-column system is tuned for similar compounds affected in a similar way by the experimental parameters or retention mechanism.

An explanation of this tuning process can be provided without referring to actual operational steps by defining "vectorial migration velocity" as the ordered pair of time averaged migration velocities, (U1, U2), on first and second chromatographic sections. If, as will generally be the case, the column lengths, or effective column lengths in a comprehensive two-dimensional gas chromatograph are constant, of lengths L1 and L2 respectively, the relation between retention time and average migration velocity is that retention time, T, equals length, L, divided by time-averaged migration velocity, V. This relationship converts a vectorial migration velocity to a vectorial retention time, (T1, T2). It is convenient to refer to a vectorial retention time as simply a "retention vector", and likewise, to refer to a vectorial migration velocity as simply a "migration vector".

With every peak resolved or even partly resolved near the end of a comprehensive two-dimensional (or higher-dimensional) gas chromatograph, there may be associated a migration vector and a retention vector. A multiplicity of peaks resolved, or nearly resolved, gives rise to a multiplicity of retention vectors and migration vectors. Given this multiplicity of vectors, it is possible to maximize various statistical measures of separation between vectors by systematically varying the experimental conditions of the chromatographic sections in time, or from one cycle of the second section to the next.

One such statistical measure would be the correlation coefficient of the least squares line through the vectors, with respect to variation of one or more experimental parameters such as temperature ramp rate, carrier flow rate, etc. Many other statistical measures of peak separation might be employed.

In this specification, the independence or differences in the effect on sample components to selectively alter their mobility is indicated by the term "specific retention difference". This term refers to an individual experimental parameter and the manner in which its effect on individual sample components differs between the first and second or subsequent sections in creating a difference in the mobility of the sample components. The final resolution at the outlet of the second or subsequent sections is directly related to the sum of these specific retention differences. Thus, maximum peak capacity or resolution occurs when the second or subsequent sections have maximum independence in experimental parameters from those of the first section and thus a maximum specific retention difference.

If a two-dimensional chromatograph is considered for simplicity, the second column is designed and operated to maximize the specific retention difference for those components not resolved when run through the first column. In the case of a column designed for detection of a specific predetermined substance, or species of substances, or an analysis of mixtures which have sufficient known similarities, the column is designed through the use of reference samples. In such a design, an attempt is made to select from known information and experimentally, the retention mechanisms that provide the best peak capacity and/or resolution in an economical system, reasonable in cost of fabrication and use. The factors include the length of sections and number of sections, as well as more easily variable experimental parameters such as temperature. In such a design, when properly tuned, the sections are as orthogonal as possible in the sense that second retention times of homologous series do not vary with first retention times, and provide the maximum benefit by maximizing independence of the experimental parameters between the two sections.

Some of the experimental parameters arise from the design, such as, for example, gas velocity may be changed between chromatographic stages by manufacturing the column in two sections having different diameters. Similarly, the stationary phase may be changed and the temperature programming altered between trial runs for tuning experimentally, or they may be selected from known information.

Further Description of Orthogonality

To improve the benefits obtainable from multiple dimension chromatography, it is desirable for the second or successive sections to independently resolve components which were not fully resolved in the first section or prior sections using retention mechanisms different from those which cause the principal resolution in the first or prior sections. In this specification, the words "retention mechanisms" are the conditions of a chromatographic medium which selectively alter the mobilities of different components of a sample therein to cause separation of components. These chromatographic conditions include carrier gas velocity, temperature, the degree of polarity of the stationary phase and the like. The words "experimental parameters" refer to controllable aspects of instrument operation which, acting together, establish or cause chromatographic conditions.

Because the components of the sample that are to be resolved in the second or subsequent sections may have been poorly resolved in the first section, experimental parameters in the second section are preferably not so similar to those in the first section as to exert only the same influence on the components. Experimental parameters of a second or subsequent section which operate differently on those sample components or operate in a manner substantially, or at least partially, independent of the mechanisms of the first section, better resolve the components that were not resolved in a satisfactory manner in the first section. The greater the degree of independence of those experimental parameters, the greater the resolution of the system oveall.

To orthogonalize a comprehensive two-dimensional gas chromatographic separation, an adjustment of experimental parameters is made in the second dimension of chromatographic separation as a function of progress of the first dimension of chromatographic separation such that substances emerging from the first dimension fall within a defined range of retention times on the second dimension. Also, or alternatively, adjustment is made such that the statistical measures of peak scatter on the second dimension is maximized. The second dimension is varied during the time of the generation of the first dimension chromatogram such that the two-dimensional chromatogram is orthogonal. The variations are created as discussed above.

In one mode of operation, experimental conditions of both sections of a comprehensive two-dimensional gas chromatograph are varied systematically in time so as to make the "peak capacity" (the number of peaks the system can resolve with unit resolution) of the chromatographic system equal to, nearly equal to, or as close as possible to the arithmetic product of the individual peak capacities of the first and second chromatographic sections. In this mode, we say again that the system is "orthogonal" or "tuned" with respect to peak capacity. The same tuning criterion can be applied to gas chromatographs having more than two sections, i.e. comprehensive three dimensional, or higher dimensional gas chromatographs.

The orthogonality of the multi-dimensional chromatogram is tuned by controlling the temperature, temperature programming rate, or carrier gas linear velocity of each dimension of chromatographic separation such that substances emerge from each dimension within desired ranges of retentions and/or with maximal statistical scatter. This tuning may be used in any method of chemical analysis comprising comprehensive multi-dimensional liquid chromatography, supercritical fluid chromatography, and/or gas chromatography in any combination connected in any sequence using analogous temperature and/or solvent programming techniques to tune the orthogonality of the separation in two or more dimensions.

The detector for detecting the components of the chromatogram may be a high-speed flame ionization detector, a high-speed thermal conductivity detector, a mass spectrometer or other vacuum system detector, or a high-speed fixed wavelength infrared absorbance detector.

Three or more dimensions of chromatographic separation may be serially connected such that each additional dimension generates multiple chromatograms at various times during the development of the previous dimension chromatogram. The comprehensive separation is created by: (1) each successive dimension of chromatographic separation being significantly faster than the previous dimension; and/or (2) the application of multiple mutually orthogonal modulation signals at the input to each dimension of chromatographic separation. In the latter case all such dimensions have similar speeds and the multi-dimensional chromatogram is computed by deconvolving the orthogonal modulation signals from the output detector signal. A component of system generates concentration pulses in a gas stream flowing through a tube. The component consists of a length of tubing in which some substances carried with the gas stream are retained for a period of time and then released as a concentration pulse compact in distance and short in duration. This is accomplished with a mechanism whereby a first portion of the length of tubing accumulates retained substances at a relatively low temperature and releases them to a second portion of the length of tubing. The substances are released as a concentration pulse, compact in distance, upon application of heat. The second portion of the tubing holds the compact concentration pulse while the first portion cools sufficiently to again retain substances. Upon application of heat the second portion accelerates the compact concentration pulse so that it moves rapidly and becomes short in duration.

The first portion of the length of tubing contains more than one stage for substance accumulation and concentration pulse compaction. The length of tubing may contain an adsorbent stationary phase in its interior and an electrically conductive layer on its exterior. Alternatively the exterior wall may be electrically conductive.

In FIG. 3, there is shown an injector 12 and source of carrier gas 13 connected together to inject sample into a column transfer line 20. The injector 12 includes a container 100, an enlarged hood 101, an optional source of heat 104 and a source of energy 102. The container 100 includes a liquid or solid 106 from which a vapor evaporates under normal vapor pressure, and is adapted for applying to the transfer line 20 a vapor indicating the contents of the sample 106 within the container 100. The source of electrical energy 102 is electrically connected to a small heater 104 to increase the vapor pressure of the compounds being analyzed within the liquid 106 and thus, increase the density of the sample applied to the injector 12.

The source of carrier gas 13, such as hydrogen or helium, is supplied from the container 13 into the container 100 which has a closed top receiving the injector hood 101 at the end of the transfer line 20 so that vapor from the liquid 106 which fills the atmospheric section 108 enters an enlarged section or hood 101 which communicates with the interior of the transfer line 20. With this arrangement, the contents of a liquid or a solid which vaporizes or sublimates ingredients in the air in a room or compartment can be sensed and analyzed to determine its content. Moreover, special analysis may be performed to find a specific peak such as ethanol, certain drugs, gas, or the like to provide sensitive and specific chemical sensors.

In FIG. 4, there is shown a simplified perspective view, partly broken away and exploded, of a chromatographic system 10C having a supporting spool 110, an insulative sheet 120 and a connector assembly 122 mounted together to receive a column 14. The column 14 is wound around the insulative sheet 120 and electrically connected through the connector assembly 122, all of which are supported on the spool 110. The insulative sheet 120 may be made of a one to 5 mil thick polyimide film sold under the trademark, Kapton, (by E. I. DuPont de Nemours and Co., Wilmington, Del.) and receives on its surface painted conductors connecting the resistive coat of the column 14 to electrical connectors within the spool 110 in a manner to be described hereinafter. A second sheet 121 could be added to cover the assembly to permit the flow of fluid over the column 14.

To support the column 14 and electrical connectors to it, the spool 110 includes first and second spool rims 116A and 116B connected by an integrally formed aluminum or nylon cylindrical tubular wall 114 recessed from its outer surface and flush with its inner surface to form a tubular inner hollow cylinder 112 extending through it along its longitudinal axis. With this arrangement, conductive leads and the like may pass through the hollow cylinder 112 and make connection with the column 14 on the outer side of the spool 110.

To make electrical connections to the column 14 which is wound around the insulative sheet 120, the spool 110 includes an axially extending slot 118 through it. The connector assembly 122 extends through the slot to connect the resistive coat of the column 14 to electrical connectors passing through the hollow cylinder 112 of the spool 110.

The connector assembly 122 includes a metal clip 124, a support body 130, conductor pins 128A and 128B and column pins, such as the one shown at 134. The metal clip 124 receives the support body 130 and the conductor pins 128A and 128B. It includes a folded over top having screw holes which receive screws 126A and 126B through corresponding tapped holes therein. The screws and holes enable the metal clip 124 to be fastened to the spool wall 114 with a portion extending through the slot 118 and containing the support body 130.

The support body 130 forms an electrical contact with the conductor pins 128A and 128B and also with the column pin 134. Column pins, such as 134, are electrically connected to the conductive coated trace lines, such as 136A, which electrically connects the conductor pin 134 to the resistive coat of the column 14 to make an electrical connection therethrough and to the conductor pins 128A and 128B.

In FIG. 5, there is shown another perspective view broken away of an embodiment of chromatographic system 10C showing the first column section 14A and second column section 14B with the numeral 14 being used to represent both sections of the column 14. The column 14 is wound around the insulative layer 120 (FIG. 4) over the spool wall 114 and between the rims 116A and 116B. The broken away portion shown in FIG. 5 reveals conductive leads 136A-136D (FIG. 6), connected to four of the column pins 134A-134D (FIG. 6), respectively, and the supporting body 130 for the purpose of making electrical connections between the column conductive resistive coat and connectors (not shown in FIG. 5) through the inner hollow cylinder 112 of the spool 110.

Figure 6:
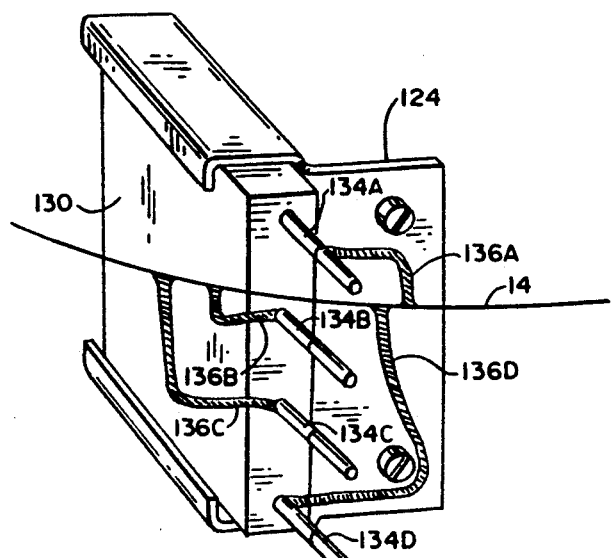
FIG. 6 is a perspective view of a portion of FIG. 5.

In FIG. 6, there is shown an enlarged perspective view of the metal clip 124 supporting the conductive body 130 illustrating the manner in which the column pins 134A-134D are electrically connected by the conductive traces 136A-136D, respectively, to sections of the column 14 and to the body 130. The electrical connections to leads within the hollow cylinder 112 are not shown in FIG. 6.

Figure 7:
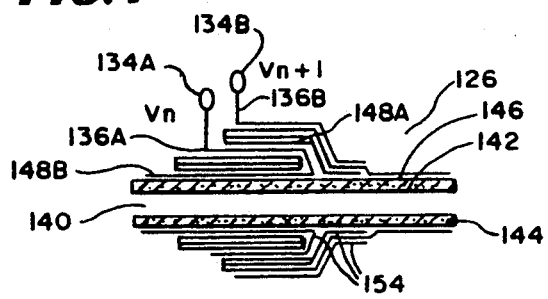
FIG. 7 is a sectional schematic view of one embodiment of a portion of a chromatographic column together with connections used in heating it.

In FIG. 7, there is shown a sectional view of a portion of a column system 14 illustrating the manner in which connection is made to the column pins such as 134A and 134B at junctions between two different resistive coats on the column system 14. As best shown in this view, the column system 14 includes an open longitudinal center 140 about a tubular cylindrical internal coat 142 applied inside the capillary column wall, a fused silica or other tubular cylindrical capillary wall 144, and external resistive coats, such as 146. There may be a plurality of such coats separated from each other, as shown at 154. As shown in this figure, two separate coats, insulated from each other, are each connected to respective ones of the column pins 134A and 134B to receive voltages. These coats overlap in the longitudinal direction.

To provide electrical connections to the coats, a thin conductive trace such as 136A and 136B can be printed or painted with metallic paint in a manner known in some fields. The adaptation of painting conductive coats to gas chromatography is described in greater detail below. The trace 136A shown in FIG. 7 is painted over the insulative sheet 120 (FIG. 4) and brought into contact with the resistive coat 146 of the column system 14 with the conductive trace 136A being separated from the conductive trace 136B. Each trace is connected to a different separated portion of the resistive coats 146 on the column system 14. Moreover, the conductive traces 136A and 136B are separated by insulators 148A and 148B which may be sheet material or thin coats or the like. The conductive traces 136A and 136B are coated to apertures which receive pins, such as 134A and 134B, to make different electrical connections with conductors.

Under some circumstances, conductive or resistive coats are overlapped as shown in FIG. 7. One such circumstance is between the first and second stages of the modulator so that the column is heated by a resistive coat in a manner that causes complete removal of coated sample upon heating so as to eliminate an area of the interior of the column between the first and second stages which collects sample and fails to release sample as a front upon heating.

To form overlapping coats, a first layer 146A of resistive paint is applied to the column such as over a polyimide coat on a capillary column from a first end point to a second end point. The first end point may be connected to a source of power, to another coat, such as 146, or to a conductive element. A first insulative layer is then applied as a coat over the first resistive layer 148A stopping short of the second end of the first resistive layer 146A so that the latter remains exposed. A second resistive layer 146B is applied over the first insulative layer 148A so that the second end point of the second resistive layer 146B makes electrical contact at the second end point of the first conductive layer 146A where the first insulative layer does not cover the first resistive layer. The first end of the second resistive layer is left exposed for further connection such as to a resistive trace 136A that is connected to an electrical conductor 134A for the application of electrical voltage and remains exposed on the first insulative layer. The remainder of the second resistive layer 146B is coated with a second insulating layer 148B that extends evenly over the second end of the first resistive layer and the second resistive layer.

On top of the second insulative layer, a third resistive layer is applied to provide connection to a different source of potential $V_{N+1}$ and extended in the opposite direction away from the second end of the first conductive layer. That third layer is covered with a third insulator (not shown in FIG. 7) except for the first and second ends, the first being connected to a resistive trace 136B or the like, and the second end left exposed for connection to ground, a source of potential, or another circuit element through another trace, connector or the like, or to a resistive coat such as 146.

The stages for the multi-stage modulator can be segmented with a plurality of overlapping conductors to provide as many stages as necessary. The stages can each be operated in succession as multiple stages or groups of stages can be operated in parallel to have the effect of a larger surface area modulator stage. Preferably, the stages are approximately 100 column diameters in length but may vary between 20 column diameters and 2,000 column diameters depending on the design of the column.

Figure 8:
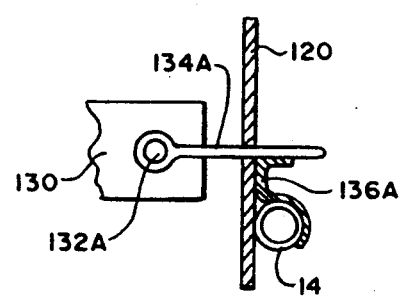
FIG. 8 is a simplified sectional view of an electrical connection used in the embodiment of FIG. 1.

In FIG. 8, there is shown a sectional view from another angle illustrating a manner in which the supporting body 130 receives the pin 134A which is connected by resistive trace 136A along the insulative Kapton sheet 120 to the resistive coats 146A and 146B (FIG. 7) on the external periphery of the column system 14 so as to make good electrical contact thereto. The contact is aided by the small sizes of the column and pin which create a meniscus around the column and the pin to form good electrical contacts thereto.

Figure 9:
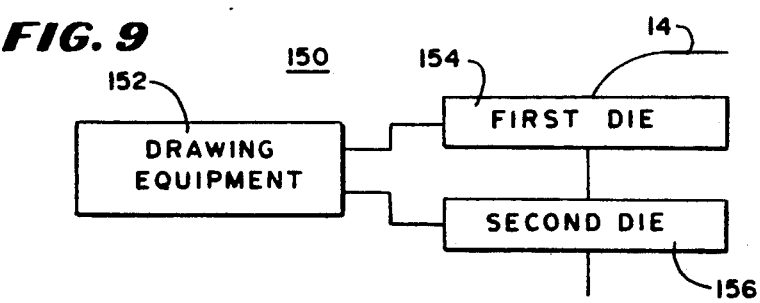
FIG. 9 is a block diagram of equipment used in making one portion of the chromatographic system of FIG. 1.

In FIG. 9, there is shown a block diagram of certain equipment useful in manufacturing the column 14, particularly when the column 14 is to have an integrally formed first column section 14A and second column section 14B of differing internal diameters. As shown in this view, fused silica drawing equipment of a conventional type 150 includes a drawing portion 152 which draws heated cylindrical tubing material through a first die 154 at a first speed to form a first diameter and then a portion of it at a second speed, possibly through a second die 156, to form a narrower diameter column.

With this arrangement, first and second columns have different retention characteristics partly because the different internal diameter columns carry the same volumetric flow volume through them. Since the volumetric flow through the two columns is the same, the linear velocity of flow of individual carrier gas and sample vapor or gas in a single direction is faster in the narrower bore.

Figure 10:
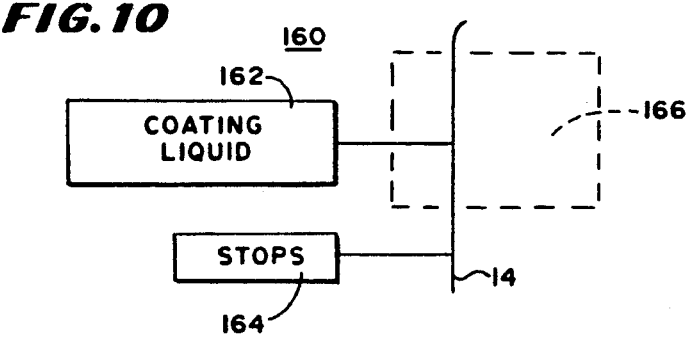
FIG. 10 is another block diagram of equipment used in making a portion of the chromatographic system of FIG. 1.

In FIG. 10, there is shown a block diagram of an internal coating apparatus 160 having a source of coating liquid 162, stops 164 for closing the column 14 and holder 166 for applying heat to enable liquid coating of the first section. This figure illustrates that sections of column having constant diameter can be internally coated with fluid coating techniques in a conventional manner individually so that a nonpolar coat, for example, can be applied to the first column and a polar coat to the second, or any other arrangements of internal coats may be used to form the stationary phase for chromatography.

From the above description, it can be understood that the technique and apparatus of this invention have several advantages over prior art gas chromatography such as providing: (1) a chromatograph which has very small size and requires very little power, so as to be portable; (2) a chromatograph which is so sensitive that it can quickly analyze trace gases in the atmosphere or those evaporated from a liquid or sublimated from a solid; (3) a chromatograph which is rapid; (4) a chromatograph which subjects substantially all sample to two, nearly independent dimensions of chromatography, (5) a system which eliminates diversion valves or butt connections between chromatographic sections or dimensions; and (6) a chromatograph which operates in successive dimensions under different conditions using different structures, phases, etc., to make a second retention time independent, or nearly so, of a first retention time, a third retention time independent from the second, and so on.

While a preferred embodiment has been described with some particularity, many modifications and variations in the preferred embodiment are possible without deviating from the invention. It is therefore to be understood that, within the scope of the appended claims, the invention may be practiced other than as specifically described.

What is claimed is:

1. A method of two-stage thermal modulation for generating concentration pulses in a gas stream flowing through a tube, said tube comprising an inlet, an outlet, a first portion which is a length of said tube comprising a first stage, and a second portion which is a length of said tube comprising a second stage, said method comprising the steps of:
    (a) creating a flow of carrier gas in a direction through said tube to produce a carrier gas flow;
    (b) introducing a sample into the carrier gas flow, said sample comprising one or more sample substances;
    (c) cooling the first stage;
    (d) cooling the second stage;
    (e) accumulating within the first stage for a period of time sample substances carried thereinto by the carrier gas, thus forming a first concentration;
    (f) heating the first stage to release the first concentration into the carrier gas flow in the form of a first concentration pulse;
    (g) carrying the first concentration pulse in said direction of carrier gas flow toward said second stage;
    (h) accumulating said first concentration pulse at the inlet of said second stage so as to focus and hold therein for a period of time, sample substances of said first concentration pulse carried by the carrier gas, thus forming a second concentration;
    (i) cooling the first stage so as to resume accumulating therein for a period of time sample substances carried thereinto by the carrier gas;
    (j) heating the second stage so as to release said second concentration into the carrier gas flow in the form of a second concentration pulse, said second concentration pulse being more compact in distance and of shorter duration than said first concentration pulse; and
    (k) cooling the second stage.

2. The method according to claim 1, wherein said first portion comprises additional stages.

3. The method according to claim 1, wherein steps (e) through (k) are repeated during the flow of the sample through the tube so as to produce a series of thermal modulations providing a series of sharp second concentration pulses.

4. The method according to claim 3, further comprising:
    detecting with a pulsed detector sample substances in said second concentration pulse emerging from the outlet of said tube; and
    synchronizing arrival of sample concentration pulses with a pulse of said detector.

5. The method according to claim 4, wherein said first portion comprises additional stages.

6. The method according to claim 4, wherein said pulsed detector is any one of a fourier transform mass spectrometer, a time-of-flight mass spectrometer, an ion-trap mass spectrometer, and a detector comprising a pulsed integrator, or a phase-locked loop.

7. The method according to claim 1, wherein said first and second stage comprise a capillary tube containing a stationary phase suitable for retaining sample substances.

8. The method according to claim 7, wherein said capillary tube comprises an external resistive coat and wherein at least one of said first and second stage is heated by passing electrical current through said external resistive coat.

9. The method according to claim 7, wherein at least one of said first and second stage comprises a conductive wall and is heated by passing an electrical current through said conductive wall.

10. The method according to claim 7, wherein at least one of said first and second stage is cooled by a Peltier heat pump.

11. The method according to claim 7, further comprising carrying said series of second concentration pulses through a final dimension of a chromatographic system which has more than one serially disposed dimension of chromatographic separation.

12. The method according to claim 11, wherein said method generates a series of sharp concentration pulses which collectively include the entire sample.

13. The method according to claim 11, wherein each of said first and second stage comprises a length of capillary column, and heating means, said heating means comprising an external resistive coat on each length of column.

14. The method according to claim 1, further comprising carrying the second concentration pulse through the tube so that the second concentration pulse emerges at the outlet of the tube, and detecting sample substances in the second concentration pulse emerging from the tube.

15. The method according to claim 1, further comprising separating said second concentration pulse into bands by chromatography.

16. A method of tuning orthogonality of a chromatographic system wherein a first dimension of chromatographic separation and a second dimension of chromatographic separation are serially disposed, said tuning comprising adjusting a retention time in said second dimension of chromatographic separation as a function of progress of said first dimension of chromatographic separation such that a statistical measure of peak scatter in a retention plane is substantially maximized, and the peak capacity of the chromatographic system approximates the arithmetic product of individual peak capacities of said first and said second dimensions of chromatographic separation.

17. The method according to claim 16, wherein substances which belong to a homologous series of compounds and are present in a sample subjected to a chromatographic separation in said chromatographic system emerge from said second dimension of chromatographic separation such that the substances belonging to the homologous series have retention times in the second dimension which are substantially equal.

18. The method of tuning orthogonality according to claim 16, wherein more than two dimensions of chromatographic separation are serially disposed thereby forming a plurality of preceding chromatographic dimensions and subsequent chromatographic dimensions, said tuning comprising an adjustment of a time of retention of each subsequent dimension of chromatographic separation as a function of progress of a preceding dimension of chromatographic separation such that the various dimensions of the multi-dimensional chromatographic system are made orthogonal.

19. The method according to claim 16, wherein at least one of said first and second dimension of chromatographic separation comprises a retention gradient.

20. The method according to claim 16, wherein said first dimension comprises a first stationary phase and said second dimension comprises a second stationary phase, said second stationary phase being serially disposed relative to and chemically distinct from said first stationary phase.

21. The method according to claim 20, wherein said first and second dimensions comprise serially connected columns containing said first and second stationary phases.

22. The method according to claim 21, wherein said first and second stationary phases are deposited serially within a single capillary column.

23. The method according to claim 16, wherein at least one of said first and second dimensions of chromatograhic separation comprises a capillary column.

24. The method according to claim 23, wherein said first and second dimensions each comprise a single stationary phase deposited within said capillary column.

25. The method according to claim 24, wherein a retention time of the second dimension is varied by varying any of:
(a) temperature of the second dimension,
(b) rate of change of temperature of the second dimension, and
(c) electromagnetic radiation applied to the second dimension.

26. The method according to claim 23, wherein said capillary column comprises a retention gradient.

27. The method according to claim 26, wherein said gradient is thermal.

28. The method according to claim 26, wherein said gradient is a gradient of stationary phase thickness within said capillary column.

29. The method according to claim 16, wherein said first and second dimensions comprise a combination of dimensions selected from liquid chromatographic, supercritical fluid chromatographic, and gas chromatographic dimensions.

30. The method according to claim 29, wherein both dimensions are gas chromatographic.

31. The method according to claim 30, wherein a dimension of chromatographic separation comprises a thermal gradient.

32. The method according to claim 31, wherein said dimension of chromatographic separation comprising the thermal gradient is said second dimension.

33. The method according to claim 30, wherein at least one of said first and second dimension of chromatographic separation is equipped with a gradient of stationary film thickness.

34. The method according to claim 33, wherein the chromatographic dimension equipped with a gradient of stationary film thickness is said second chromatographic dimension.

35. The method according to claim 30, wherein tuning a two-dimensional gas chromatograph comprises variation of a temperature of the second chromatographic dimension as a function of progress on the first chromatographic dimension.

36. The method according to claim 35, wherein said first and second chromatographic dimensions are housed in a single oven.

37. The method according to claim 35, wherein the two-dimensional gas chromatograph is tuned through choice of relative column lengths, column diameters, stationary phase thicknesses, thickness gradients, carrier gas linear velocities, and a temperature program.

38. The method according to claim 35, wherein substantially all of the effluent from the first chromatographic dimension enters the second.

39. The method according to claim 35, wherein said second dimension of chromatographic separation comprises a capillary column, and the temperature of the column is varied by varying electrical current through a resistive coat on the column exterior.

40. The method according to claim 39, wherein substantially all of the effluent from the first chromatographic dimension enters the second.

41. The method according to claim 30, wherein said tuning orthogonality of the two-dimensional gas chromatograph comprises varying a linear velocity of the carrier gas in the second chromatographic dimension as a function of progress of the first chromatographic dimension.

42. The method according to claim 41, wherein relative column lengths, column diameters, stationary phase thicknesses, and temperatures are chosen such that a programmed variation of a linear carrier gas velocity in the first chromatographic dimension causes a variation of said linear velocity of the carrier gas in the second chromatographic dimension.

43. The method according to claim 29, wherein at least one of said first and second dimension of chromatographic separation comprises a retention gradient.

44. A method of two-dimensional chromatography comprising the steps of:
(a) injecting a sample composed of one or more sample substances into a first dimension of chromatographic separation;
(b) carrying said sample along said first dimension of chromatographic separation in a direction so as to cause a first resolution of said sample into a series of bands;
(c) carrying said sample into a two-stage thermal modulator comprising a first stage and a second stage;
(d) cooling said first stage;
(e) cooling said second stage;
(f) accumulating a portion of the sample between said first dimension of chromatographic separation and a second dimension of chromatographic separation disposed in serial relationship with said first dimension of chromatographic separation, said accumulating comprising generating concentration pulses within said two-stage thermal modulator, wherein said generating concentration pulses comprises
(I) accumulating within the first stage for a period of time sample substances carried thereinto from the first dimension, thus forming a first concentration,
(II) heating the first stage to release the first concentration in said direction in the form of a first concentration pulse,
(III) carrying the first concentration pulse in said direction toward said second stage,
(IV) accumulating said first concentration pulse at an inlet of said second stage so as to focus and hold in the second stage, for a period of time, sample substances of said first concentration pulse thus forming a second concentration, (V) cooling the first stage so as to resume accumulating therein for a period of time sample substances carried thereinto by the carrier gas;

(g) transmitting the accumulated portion of sample as a sharp wave front to an inlet of the second dimension of chromatographic separation by heating the second stage so as to release said second concentration into the carrier gas flow in the form of a second concentration pulse, said second concentration pulse being more compact in distance and of shorter duration than said first concentration pulse;

(h) cooling the second stage; and (i) carrying the portion of sample along the second dimension of chromatographic separation so as to cause a further resolution of said portion of sample;

repeating steps (f)–(i), so as to generate a multiplicity of said sharp wave fronts and a multiplicity of said further resolutions without materially changing said first resolution; and detecting said multiplicity of further resolutions with a first detector so as to generate a multiplicity of second dimension chromatograms together comprising a two-dimensional chromatogram of said sample.

45. The method according to claim 44, further comprising splitting off a portion of effluent from a first dimension of chromatographic separation for detection by an additional detector located near the junction between chromatographic dimensions, and wherein said repeating causes substantially the remainder of sample not split off to said additional detector to be submitted to the second dimension of chromatographic separation.

46. The method according to claim 44, wherein said repeating causes substantially the entire sample to be submitted to the second dimension of chromatographic separation.

47. The method according to claim 44, further comprising carrying said sample through at least one additional dimension of chromatographic separation.

48. A method of two-dimensional chromatographic separation comprising the steps of:

(a) injecting a sample composed of various sample substances into a first dimension of chromatographic separation;

(b) carrying said sample along said first dimension of chromatographic separation so as to cause a first resolution of said sample into a series of bands;

(c) accumulating a portion of the sample between said first dimension of chromatographic separation and a second dimension of chromatographic separation disposed in serial relationship with said first dimension of chromatographic separation;

(d) transmitting the accumulated portion of sample as a sharp wave front to an inlet of the second dimension of chromatographic separation;

(e) carrying the portion of sample along the second dimension of chromatographic separation so as to cause a further resolution of said portion of sample; and repeating steps (c), (d), and (e) so as to generate a multiplicity of said sharp wave fronts and a multiplicity of said further resolutions by said second dimension of chromatographic separation, without materially changing said first resolution;

detecting said multiplicity of further resolutions so as to generate a multiplicity of second dimension chromatograms together comprising a two-dimensional chromatogram of said sample; and tuning the orthogonality of said two-dimensional chromatographic separation by a method wherein said first dimension of chromatographic separation and said second dimension of chromatographic separation are serially disposed, said tuning comprising adjusting a retention time in said second dimension of chromatographic separation as a function of progress of said first dimension of chromatographic separation such that a statistical measure of peak scatter in a retention plane is substantially maximized, and the peak capacity of the chromatographic system approximates the arithmetic product of individual peak capacities of said first and said second dimension of chromatographic separation.

49. The method according to claim 48, wherein said repeating causing substantially the entire sample to be submitted to the second dimension of chromatographic separation.

50. The method according to claim 48, further comprising carrying said sample through at least one additional dimension of chromatographic separation.

51. The method according to claim 48, further comprising splitting off a portion of effluent from said first dimension of chromatographic separation for detection by an additional detector located near a junction of chromatographic dimensions, and wherein said repeating causes substantially the remainder of sample not split off to said additional detector to be submitted to the second dimension of chromatographic separation.

52. The method according to claim 48, wherein at least one of said first and second dimension of chromatographic separation comprises a retention gradient.

53. The method according to claim 48, wherein said first dimension comprises a first stationary phase and said second dimension comprises a second stationary phase, said second stationary phase being serially disposed relative to and chemically distinct from said first stationary phase.

54. The method according to claim 53, wherein said first and second dimensions comprise serially connected columns containing said first and second stationary phases.

55. The method according to claim 53, wherein said first and second stationary phases are deposited serially within a single column.

56. The method according to claim 48, wherein at least one of said first and second dimensions of chromatographic separation comprises a capillary column.

57. The method according to claim 56, wherein said first and second dimensions each comprise a single stationary phase deposited within said capillary column.

58. The method according to claim 57, wherein a retention time of the second dimension is varied by varying any of:

(a) temperature of the second dimension, (b) rate of change of temperature of the second dimension, and (c) electromagnetic radiation applied to the second dimension.

59. The method according to claim 56, wherein said capillary column comprises a retention gradient.

60. The method according to claim 59, wherein said gradient is thermal.

61. The method according to claim 59, wherein said gradient is a gradient of stationary phase thickness within said capillary column.

62. The method according to claim 48, wherein said first and second dimensions comprise a combination of dimensions selected from liquid chromatographic, supercritical fluid chromatographic, and gas chromatographic dimensions.

63. The method according to claim 62, wherein both dimensions are gas chromatographic.

64. The method according to claim 63, wherein a dimension of chromatographic separation comprises a thermal gradient.

65. The method according to claim 64, wherein said dimension of chromatographic separation comprising the thermal gradient is said second dimension.

66. The method according to claim 63, wherein at least one of said first and second dimension of chromatographic separation is equipped with a gradient of stationary film thickness.

67. The method according to claim 66, wherein the chromatographic dimension equipped with a gradient of stationary film thickness is said second chromatographic dimension.

68. The method according to claim 63, wherein tuning a two-dimensional gas chromatograph comprises variation of the temperature of the second chromatographic dimension as a function of progress on the first chromatographic dimension.

69. The method according to claim 68, wherein said first and second chromatographic dimensions are housed in a single oven.

70. The method according to claim 68, wherein the two-dimensional gas chromatograph is tuned through choice of relative column lengths, column diameters, stationary phase thicknesses, thickness gradients, carrier gas linear velocities, and a temperature program.

71. The method according to claim 68, wherein substantially all of the effluent from the first chromatographic dimension enters the second.

72. The method according to claim 68, wherein said second dimension of chromatographic separation comprises a capillary column, and a temperature of the column is varied by varying electrical current through a resistive coat on the column exterior.

73. The method according to claim 72, wherein substantially all of the effluent from the first chromatographic dimension enters the second chromatographic dimension.

74. The method according to claim 63, wherein said tuning orthogonality of the two-dimensional gas chromatograph comprises varying a linear velocity of the carrier gas in the second chromatographic dimension as a function of progress of the first chromatographic dimension.

75. The method according to claim 74, wherein relative column lengths, column diameters, stationary phase thicknesses, and temperatures are chosen such that a programmed variation of a linear carrier gas velocity in the first chromatographic dimension causes said varying of said linear velocity of the carrier gas in the second dimension.

76. The method according to claim 62, wherein at least one of said first and second dimension of chromatographic separation comprises a retention gradient.

77. An apparatus for generating a concentration pulse of a sample, said apparatus comprising:

a tube having an inlet, an outlet, a first portion which is a length of said tube comprising a first stage, and a second portion which is a length of said tube comprising a second stage;

means for creating a flow of carrier gas in a direction through said tube to produce a carrier gas flow;

means for introducing a sample into the carrier gas flow, said sample comprising one or more sample substances;

means for cooling the first stage;

means for cooling the second stage;

means accumulating within the first stage for a period of time sample substances carried thereinto by the carrier gas, thus forming a first concentration;

means for heating the first stage to release the first concentration into the carrier gas flow in the form of a first concentration pulse;

means for carrying the first concentration pulse in said direction of carrier gas flow toward said second stage;

means for accumulating said first concentration pulse at the inlet of said second stage so as to focus and hold therein for a period of time, sample substances of said first concentration pulse carried by the carrier gas, thus forming a second concentration;

means for cooling the first stage so as to resume accumulating therein for a period of time sample substances carried thereinto by the carrier gas;

means for heating the second stage so as to release said second concentration into the carrier gas flow in the form of a second concentration pulse, said second concentration pulse being more compact in distance and of shorter duration than said first concentration pulse; and means for cooling the second stage.

78. The apparatus according to claim 77, wherein said first portion comprises additional stages.

79. The apparatus according to claim 77, wherein said first and second stage comprise a capillary tube containing a stationary phase suitable for retaining sample substances.

80. The apparatus according to claim 79, wherein said capillary tube comprises an external resistive coat and wherein at least one of said first and second stage is heated by passing electrical current through said external resistive coat.

81. The apparatus according to claim 79, wherein at least one of said first and second stage comprises a conductive wall and is heated by passing an electrical current through said conductive wall.

82. The apparatus according to claim 79, wherein at least one of said means for cooling the first stage and said means for cooling the second stage is a Peltier heat pump.

83. The apparatus according to claim 79, further comprising a final dimension of a chromatographic system which has more than one serially disposed dimension of chromatographic separation.

84. The apparatus according to claim 77, further comprising a detector at the outlet of the tube for detecting sample substances in the second concentration pulse emerging from the tube.

85. The apparatus according to claim 84, wherein said detector is a pulsed detector.

86. The apparatus according to claim 85, wherein said pulsed detector is any one of a fourier transform mass spectrometer, a time-of-flight mass spectrometer, an ion-trap mass spectrometer, and a detector comprising a pulsed integrator, or a phase-locked loop.

87. The apparatus according to claim 77, wherein each of said first and second stage comprises a length of capillary column, and said heating means for said first stage and said heating means for said second stage comprise an external resistive coat on each length of column.

88. The method according to claim 77, wherein said first portion comprises additional stages.

* * * * *